(12) United States Patent
Huang et al.

(10) Patent No.: US 8,703,438 B2
(45) Date of Patent: Apr. 22, 2014

(54) LIGAND BINDING STABILIZATION METHOD FOR DRUG TARGET IDENTIFICATION

(75) Inventors: Jing Huang, Los Angeles, CA (US); Brett Eugene Lomenick, Los Angeles, CA (US); Rui Hao, Los Angeles, CA (US); Nao Jonai, Yokohama (JP); Thomas M. Vondriska, Los Angeles, CA (US); Sarah Warburton, Los Angeles, CA (US); Gregory Joseph Baker, Los Angeles, CA (US); Mariam Aghajan, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 710 days.

(21) Appl. No.: 12/621,290

(22) Filed: Nov. 18, 2009

(65) Prior Publication Data

US 2010/0184112 A1      Jul. 22, 2010

Related U.S. Application Data

(60) Provisional application No. 61/115,890, filed on Nov. 18, 2008.

(51) Int. Cl.
   *C12Q 1/37*      (2006.01)
(52) U.S. Cl.
   USPC .......................................................... 435/23
(58) Field of Classification Search
   USPC .......................................................... 435/23
   See application file for complete search history.

(56) References Cited

U.S. PATENT DOCUMENTS

| | | | |
|---|---|---|---|
| 6,395,889 B1 * | 5/2002 | Robison | 536/23.2 |
| 7,288,382 B2 * | 10/2007 | Harbury et al. | 435/7.1 |
| 2009/0238808 A1 * | 9/2009 | Drewes et al. | 424/94.1 |

OTHER PUBLICATIONS

Nishiya Y. et al. Drug Target Identification From Total Cellular Lysate by Drug Induced Conformational Changes. Analytical Biochemistry 385:314-320, Dec. 2008.*
Banaszynski et al. (2006) "A Rapid, Reversible, and Tunable Method to Regulate Protein Function in Living Cells Using Synthetic Small Molecules" *Cell* 126: 995-1004.
Cohen et al. (2008) "Dynamic Proteomics of Individual Cancer Cells in Response to a Drug" *Science* 322(5907): 1511-1516.
Nishiya et al. (2009) "Drug—target identification from total cellular lysate by drug-induced conformational changes" *Anal. Biochem.* 385: 314-320.
Park et al. (2007) "Energetics-based protein profiling on a proteomic scale: identification of proteins resistant to proteolysis" *J Mol Biol* 368: 1426-1437.
Stankunas et al. (2003) "Conditional Protein Alleles Using Knockin Mice and a Chemical Inducer of Dimerization" *Mol Cell* 12: 1615-1624.
Teesdale-Spittle (2008) "In Search of Biological Activity" *Chem. in New Zealand* 138-143.
Wijayaratne et al. (2001) "The Human Estrogen Receptor-α Is a Ubiquitinated Protein Whose Stability Is Affected Differentially by Agonists, Antagonists, and Selective Estrogen Receptor Modulators" *J Biol Chem* 276: 35684-35692.

* cited by examiner

*Primary Examiner* — Ralph Gitomer
(74) *Attorney, Agent, or Firm* — Tom Hunter; Weaver Austin Villeneuve & Sampson LLP

(57) ABSTRACT

Drug affinity responsive target stability (DARTS) is a method of drug target ID with several significant advantages over current techniques. In certain embodiments the method involves contacting a sample comprising one or more protein target(s) with a test agent to form a sample/test agent mixture; contacting the mixture with a protease; and identifying a protein or protein fragment that is protected from proteolysis, wherein the protection from proteolysis is an indicator that the protein or protein fragment binds to or interacts with the test agent.

36 Claims, 18 Drawing Sheets

SEQUENCE LISTING

<160> NUMBER OF SEQ ID NOS: 10

<210> SEQ ID NO 1
<211> LENGTH: 24
<212> TYPE: PRT
<213> ORGANISM: Homo sapiens

<400> SEQUENCE: 1

Ile Gln Gln Arg Ala Ile Ile Pro Cys Ile Lys Gly Tyr Asp Val Ile
1               5                   10                  15

Ala Gln Ala Gln Ser Gly Thr Gly
            20

<210> SEQ ID NO 2
<211> LENGTH: 24
<212> TYPE: PRT
<213> ORGANISM: Mus musculus

<400> SEQUENCE: 2

Ile Gln Gln Arg Ala Ile Leu Pro Cys Ile Lys Gly Tyr Asp Val Ile
1               5                   10                  15

Ala Gln Ala Gln Ser Gly Thr Gly
            20

<210> SEQ ID NO 3
<211> LENGTH: 24
<212> TYPE: PRT
<213> ORGANISM: Xenopus laevis

<400> SEQUENCE: 3

Ile Gln Gln Arg Ala Ile Met Pro Cys Ile Lys Gly Tyr Asp Val Ile
1               5                   10                  15

Ala Gln Ala Gln Ser Gly Thr Gly
            20

<210> SEQ ID NO 4
<211> LENGTH: 24

```
<212> TYPE: PRT
<213> ORGANISM: Drosophila melanogaster

<400> SEQUENCE: 4

Ile Gln Gln Arg Ala Ile Ile Pro Cys Val Arg Gly Arg Asp Val Ile
1               5                   10                  15

Ala Gln Ala Gln Ser Gly Thr Gly
            20

<210> SEQ ID NO 5
<211> LENGTH: 24
<212> TYPE: PRT
<213> ORGANISM: Caenorhabditis elegans

<400> SEQUENCE: 5

Ile Gln Lys Arg Ala Ile Val Pro Cys Thr Thr Gly Lys Asp Val Ile
1               5                   10                  15

Ala Gln Ala Gln Ser Gly Thr Gly
            20

<210> SEQ ID NO 6
<211> LENGTH: 24
<212> TYPE: PRT
<213> ORGANISM: Strongylocentrotus purpuratus

<400> SEQUENCE: 6

Ile Gln Gln Arg Ala Ile Leu Pro Cys Cys Glu Gly Lys Asp Val Ile
1               5                   10                  15

Ala Gln Ala Gln Ser Gly Thr Gly
            20

<210> SEQ ID NO 7
<211> LENGTH: 24
<212> TYPE: PRT
<213> ORGANISM: Chlamydomonas reinhardtii

<400> SEQUENCE: 7

Ile Gln Gln Arg Ala Val Leu Pro Ile Val Gln Gly Arg Asp Val Ile
1               5                   10                  15

Ala Gln Ala Gln Ser Gly Thr Gly
            20

<210> SEQ ID NO 8
<211> LENGTH: 24
<212> TYPE: PRT
<213> ORGANISM: Arabidopsis thaliana

<400> SEQUENCE: 8

Ile Gln Gln Arg Gly Ile Val Pro Phe Cys Lys Gly Leu Asp Val Ile
1               5                   10                  15

Gln Gln Ala Gln Ser Gly Thr Gly
            20

<210> SEQ ID NO 9
<211> LENGTH: 24
<212> TYPE: PRT
<213> ORGANISM: Hemiselmis andersenii

<400> SEQUENCE: 9

Ile Gln Gln Lys Gly Ile Leu Pro Ile Ile His Lys Lys Asp Leu Ile
1               5                   10                  15

Ala Gln Ala Gln Ser Gly Thr Gly
            20
```

```
<210> SEQ ID NO 10
<211> LENGTH: 24
<212> TYPE: PRT
<213> ORGANISM: Saccharomyces cerevisiae

<400> SEQUENCE: 10

Ile Gln Gln Arg Ala Ile Met Pro Ile Ile Glu Gly His Asp Val Leu
1               5                   10                  15

Ala Gln Ala Gln Ser Gly Thr Gly
            20
```

LIGAND BINDING STABILIZATION METHOD FOR DRUG TARGET IDENTIFICATION

CROSS-REFERENCE TO RELATED APPLICATIONS

This application claims benefit of and priority to U.S. Ser. No. 61/115,890, filed on Nov. 18, 2008, which is incorporated herein by reference in its entirety for all purposes.

STATEMENT OF GOVERNMENTAL SUPPORT

This invention was made with Government support under Grant No. CA124974 awarded by the National Institutes of Health. The Government has certain rights in the invention.

BACKGROUND

Identification of relevant drug targets is a vital step in the drug discovery and validation process. This is particularly important because many drugs have multiple intracellular targets, some of which are relevant for the activities of the drugs and others of which may be irrelevant and may in fact be responsible for the undesirable side effects of the drugs. Identification of relevant targets can often lead to the identification of more specific drugs with fewer side effects. In many cases, drug-target identification can be complicated and act as a bottleneck to drug marketing. One of the limiting steps in this process is the need to perform structure-activity relationship studies that can be time-, money-, and labor-intensive.

Current affinity-based target identification techniques are limited by the necessity to modify each drug individually (without losing bioactivity), while indirect, non-affinity based approaches are dependent on the drug's ability to induce specific biochemical or cellular readouts (Giaever et al. (1999) *Nat Genet.* 21: 278-283; Hughes et al. (2000) *Cell* 102: 109-126)

Affinity-based methods include matrix-based affinity detection and matrix-free affinity labeling. Matrix-based affinity detection fuses the small molecule of interest to a solid support or capturable moiety such as biotin. Such matrix-based methods typically require three basic conditions: 1) that the small molecule contains a derivatizable functionality, 2) that bioactivity/binding specificity of the small molecule is unaffected by the derivatization, and 3) that the matrix does not hinder the binding of target protein to drug. The latter two criteria cannot be predicted a priori. Matrix-free affinity labeling relies on the incorporation of radioisotope, photo-reactive or fluorescent labels into the small molecule of interest and must typically also satisfy criteria one and two above. In both affinity chromatography and matrix-free methods, proteins are incubated with the modified small molecule and the binding proteins are revealed by mass spectrometry following gel electrophoresis. Genetic and other versions of matrix-based affinity chromatography, e.g., yeast three-hybrid (Licitra and Liu (1996) *Proc. Natl. Acad. Sci.*, USA, 93: 12817-12821) and phage display cloning (Sche et al. (1999) *Chem Biol* 6: 707-716), require tagged small molecules as well. Thus current affinity methods are limited to small molecules that contain derivatizable functionalities and whose bioactivity/binding is unaffected by the modification Indirect, non-affinity based approaches, which infer drug targets/pathways from the physiological responses or biochemical signatures the drugs produce, have also been developed. For example, classical genetics relies on the isolation of drug-resistant mutations (Heitman et al. (1991) *Science* 253: 905-909) or gene dosage effects (Rine et al. (1983) *Proc. Natl. Acad. Sci.*, USA, 80: 6750-6754), and several genome-wide methods also rely on fitness changes (Giaever et al. (1999) *Nat Genet.* 21: 278-283; Lum et al. (2004) *Cell* 116: 121-137; Parsons et al. (2004) *Nat Biotechnol* 22: 62-69; Luesch et al. (2005) *Chem Biol* 12: 55-63; Butcher et al. (2006) *Nat Chem Biol* 2: 103-109). An inherent limitation of these methods is that they are applicable only to drugs that affect cell growth/viability. Another powerful approach, genome-wide expression profiling (Hughes et al. (2000) *Cell* 102: 109-126; Lamb et al. (2006) *Science* 313: 1929-1935), on the other hand, is applicable only to drugs that induce major transcriptome changes. These genetic and large-scale "omic" profiling approaches are also primarily limited to yeast or other simple, well-characterized model organisms. Moreover, the "readout" is often far downstream from the drug target.

DEFINITIONS

The terms "polypeptide", "peptide" and "protein" are used interchangeably herein to refer to a polymer of amino acid residues.

The term "test agent" refers to an agent that is to be screened in one or more of the assays described herein. The agent can be virtually any chemical compound. It can exist as a single isolated compound or can be a member of a chemical (e.g. combinatorial) library. In certain embodiments the "test agent" is a human or veterinary pharmaceutical. In various embodiments the test agent is a pharmaceutical listed in the Merck Index 14th Edition. In certain embodiments the test agent includes, but is not limited to, a metabolite, a herbal or other plant extract, a food component, a food additive, an agricultural pesticide or herbicide, a preservative, a colorant, a fragrance, an environmental agent, and a nanoparticle.

The phrase "protected from proteolysis" when referring to a protein bound by or interacting with a test agent indicates that the protein is less susceptible to proteolysis by one or more proteases in the presence of the test agent than in the absence of the test agent.

The phrase "binding or interaction with a test agent" when used with respect to a protein indicates that the test agent increases or decreases the susceptibility of the protein to proteolysis. This can be by essentially any mechanism. For example, it can be direct by binding to and thereby stabilizing the protein or indirect, e.g. by interacting with and thereby altering the conformation of the protein.

A "protease" refers to any of various enzymes, including the endopeptidases and exopeptidases, that catalyze the hydrolytic breakdown of proteins into peptides or amino acids.

SUMMARY

Identifying the molecular targets for the beneficial or detrimental effects of small molecule drugs is an important and currently unmet challenge. In various embodiments, methods are provided for identification of protein targets for drugs and other test agents. Accordingly, in certain embodiments, methods of identifying or confirming a protein target that interacts with or is bound by a test agent are provided. The methods typically involve contacting a sample comprising the protein target with the test agent to form a sample/test agent mixture; contacting mixture with a protease; and identifying a protein or protein fragment that is protected from proteolysis, where protection from proteolysis is an indicator that the protein or protein fragment binds to or interacts with the test agent. In certain embodiments the method involves scoring a protein or protein fragment that is protected from proteolysis as a potential target for the test agent(s).

In certain embodiments methods of identifying or confirming a protein target that interacts with or is bound by a test agent are provided where the methods involve contacting a sample comprising the protein target with the test agent to form a sample/test agent mixture; contacting the mixture with a protease; and identifying a protein or protein fragment whose proteolysis is increased, wherein an increase in susceptibility to proteolysis is an indicator that said protein or protein fragment binds to or interacts with said test agent. In certain embodiments the method involves scoring a protein or protein fragment whose proteolysis is increased as a potential target for the test agent(s).

In various embodiments the sample comprises one or more recombinantly expressed proteins. In certain embodiments the sample comprises a cell or tissue lysate (e.g., a cell or tissue lysate from a healthy cell or tissue, a cell or tissue lysate from a diseased cell or tissue; a cell or tissue lysate from a cell or tissue having a mutated or abnormal genome, and the like). In certain embodiments the sample comprises one or more proteins selected from the group consisting of a human protein, a non-human mammalian protein, an insect protein, a fungal protein, an algal protein, a plant protein, a bacterial protein, and a viral protein. In certain embodiments the sample comprises one or more in vitro translated protein(s). In various embodiments the in vitro translated proteins are produced in a system selected from the group consisting of a reticulolycte cell-free system, a wheat germ cell free system, and an *E. coli* cell free system. Essentially any protease can be used. In certain embodiments the protease comprises a protease selected from the group consisting of a serine protease, a threonine protease, a cysteine protease, an aspartate protease, a metalloprotease, and a glutamic acid protease. In various embodiments the protease can comprise a mixture of one or more endopeptidases and/or exopeptidases. In certain embodiments the protease comprises subtilisin, and/or thermolysin, and/or PRONASE®.

In certain embodiments the identifying comprises one or more method(s) selected from the group consisting of a 1D electrophoresis, a 2-D electrophoresis, a chromatography, a capillary electrophoresis, a Western blot, and a mass spectrograph. In certain embodiments the identifying comprises 1D or 2D SDS PAGE and staining, and optionally further comprises removing a band of the SDS page gel that shows altered protein abundance and performing mass spectrograph on the protein from the band. In certain embodiments the identifying comprises comparing the abundance of a protein contacted with the test agent to the abundance of a protein in not contacted with the test agent.

In various embodiments one test agent or a plurality of test agents can be contacted with the protein(s). In certain embodiments the test agent is a human or veterinary pharmaceutical. In certain embodiments the test agent is selected from the group consisting of a metabolite, a herbal or other plant extract, a food component, a food additive, an agricultural pesticide or herbicide, a preservative, a colorant, a fragrance, an environmental agent, and a nanoparticle.

BRIEF DESCRIPTION OF THE DRAWINGS

FIG. 2A: Scheme of DARTS. FIG. 2B: Proof of principle. Recombinant human FKBP12 was incubated with indicated drugs and digested with subtilisin. FIG. 2C: DARTS with a micromolar mTOR kinase inhibitor (E4). Arrow, recombinant human TOR fragments protected from thermolysin proteolysis; *, non-specific band.

FIG. 3A: Intact Jurkat cells were treated with DB (1 µg/mL), and lysates were subjected to thermolysin digestion and Coomassie (SimplyBlue)-staining. FIG. 3B: Enrichment of EF-1alpha isoforms in the protected band from FIG. 3A revealed by mass spectrometry analysis (SI). Red, protein enriched >2-fold with p-value <0.001; green, protein depleted >2-fold with p-value <0.001; blue, unchanged protein. FIG. 3C: DARTS detection via immunoblotting. GAPDH was resistant to thermolysin under the condition and served as a loading indicator.

FIG. 4A: Chemical structure of resveratrol. FIG. 4B: Yeast cell lysates and human HeLa cell lysates were each treated with resveratrol in vitro followed by thermolysin digestion and silver staining. Protected bands of similar size were detected. FIG. 4C: Resveratrol protects TAP-tagged eIF4A, but not an unrelated Htb2, protein from proteolysis. Arrow: protein protected from subtilisin proteolysis (*H. sapiens* (SEQ ID NO:1), *M. musculus* (SEQ ID NO:2), *X. laevis* (SEQ ID NO:3), *D. melanogaster* (SEQ ID NO:4), *C. elegans* (SEQ ID NO:5), *S. purpuratus* (SEQ ID NO:6), *C. reinhardtii* (SEQ ID NO:7), *A. thaliana* (SEQ ID NO:8), *H. andersenii* (SEQ ID NO:9), *S. cerevisiae* (SEQ ID NO:10)). FIG. 4D: Resveratrol inhibits eIF4A-dependent translation in HEK 293 cells as assayed by bicistronic translation reporters. The EMCV IRES requires the eIF4A and eIF4G subunits of eIF4F whereas the HCV IRES does not (Bordeleau et al. (2005) *Proc. Natl. Acad. Sci., USA,* 102: 10460-10465). FIG. 4E: eIF4A is required for longevity in resveratrol-treated animals. Resveratrol (50 µM) lengthens the lifespan of wild-type N2 worms fed control (gfp) RNAi (green), but not worms fed eIF4A (inf-1) RNAi (red) or daf-16 RNAi (blue). gfp(RNAi), $m_{Veh}$=19 (n=74), $m_{RSV}$=20 (n=78), P=0.0006***; inf-1(RNAi), $m_{Veh}$=26 (n=76), $m_{RSV}$=24 (n=79), P=0.4687; daf-16(RNAi), $m_{Veh}$=17 (n=78), $m_{RSV}$=17 (n=76), P=0.3305. m, mean lifespan (days of adulthood); n, number of animals tested.

FIG. 5A: Plasmid cDNA is used to program in vitro transcription/translation (IVT) for DARTS. FIG. 5B: FKBP12-rapamycin protects translated mTOR fragment in DARTS. Streptavidin-HRP was used to detect biotin-Lys incorporated into the translation product. β-actin was less susceptible to thermolysin under the condition and served as loading indicator. FIG. 5C: DARTS with IVT FLAG-tagged mTOR.

DETAILED DESCRIPTION

In various embodiments methods are provided herein that enable a universally applicable target identification approach that identifies protein targets that bind to or interact with drugs or other moieties of interest. Because the methods described herein, termed DARTS (drug affinity responsive target stability), are not limited by synthetic chemistry and are independent of any biological effects of the drug (save its binding to or interacting with the target protein(s)), they can potentially be used to identify the protein target for any moiety of interest (e.g., small organic molecule, drug, etc.).

Figure 1:
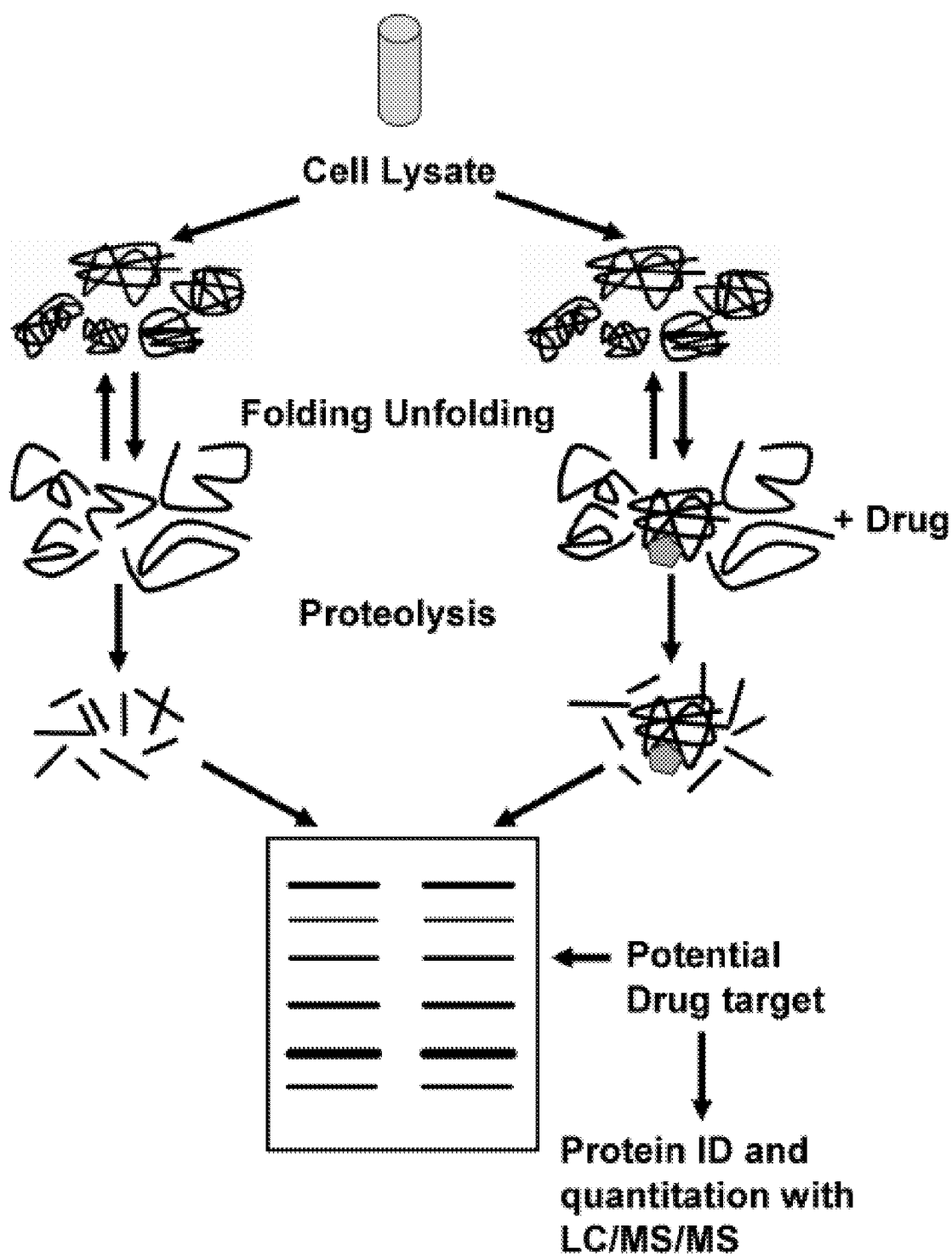
FIG. 1 schematically illustrates one embodiment of the DARTs protocol.

In one embodiment, illustrated schematically in FIG. 1, DARTS exploits the idea that ligand binding stabilizes target protein structure, thereby protecting it from proteolysis. Limited proteolysis is performed on samples comprising possible target protein(s), such as cell or tissue lysates, that differ only by the presence or absence of the test agent (e.g., drug). Protein abundance of the samples is then compared to identify potential drug binders/interactors. Where the protein binds or closely interacts with the drug, the protein structure is stabilized and become more resistant to proteolysis. The abundance of the binding/interacting protein will be greater than that amount observed in a similarly treated sample without the test agent(s). Initial analysis of protein abundance changes can, for example, be determined performed by separating the samples post-proteolysis with 1D or 2D SDS-PAGE gels and staining (e.g., with silver, coomassie blue, sypro, and the like). Any bands that appear enriched or depleted in the drug-containing sample after proteolysis can be cut out for subsequent protein identification and quantification by mass spectrometry (FIG. 1).

While drug binding is expected to protect its target protein from proteolysis in the majority of situations, it is theoretically possible that some drugs (or other test agents) may destabilize the protein, leading to increased degradation. In this instance, proteins that are depleted after proteolysis as compared to the untreated proteins are identified as binding or interacting with the test agent( ). Without being bound to a particular theory, in one mechanism underlying this approach, the binding of a drug to its target induces a localized conformational "opening" of the target protein. This conformational derangement results in the exposure of the protease recognition site(s) to cellular or exogenously added proteases. Localized proteolytic attack then results in further opening of the target protein, leading to further proteolytic degradation. Ultimately, this can result in a total proteolytic degradation of the target protein.

Thus, in one approach, protein targets of the drugs or other test agents are identified by increased abundance (e.g., where binding stabilized the protein and increases resistance to proteolysis), while in another approach, protein targets of the drugs or other test agents are identified by decreased abundance (e.g., where binding destabilizes the protein and increases susceptibility to proteolysis).

DARTS is unique because it can analyze direct binding/interaction using the native, non-derivatized test agent(s) (e.g., drugs). DAFTS is not limited by the drug's mechanism of action or ability to induce significant transcription, growth, other phenotypic changest. Nor is it limited to a single biological organism or system. Thus, it represents a universal target ID method.

In certain embodiments, DARTS methods can be used to identify the molecular targets of any or all drugs currently in clinical use, or new drugs being developed, or any molecule/agent of interest. Thus, for example, DARTS can be used to identify the targets of small molecules of relevance to human (or non-human/veterinary) health and disease including, but not limited to metabolites, herbal or other plan extracts, food components, environmental agents, new materials including various nanoparticles, and the like.

Furthermore, since drugs other agents of interest typically bind only a single domain or portion of a target protein, DARTS can be useful for foot printing experiments where the binding domain is protected from proteolysis while the rest of the protein is either unaffected or destabilized. Mass spectrometry, or other methods can then identify which portion of the protein is bound by the drug based on the peptides present in the protected portion of the target.

Target Samples.

The DARTS methods described herein can be used with essentially any sample containing or believed to contain one or more target proteins of interest. Such samples include, but are not limited to cells (e.g., unpassaged explants, cells passaged in culture, and the like). cell or tissue lysates, recombinant proteins, in vitro translated proteins, and the like. In certain embodiments the cells, cell or tissue lysates, in vivo translated proteins, and the like are derived from healthy cells (e.g., differentiated cells, totipotent cells, etc.), while in other embodiments, the they are derived from diseased cells (e.g., tumor cells, cells from neurological tissue of subjects that have Alzheimer's disease or dementia), cells obtained from subjects subject to alcohol or drug addiction, subjects having autoimmune disease and the like.

In certain embodiments the sample comprises one or more proteins selected from the group consisting of a human protein, a non-human mammalian protein, an insect protein, a fungal protein, an algal protein, a plant protein, a bacterial protein, and a viral protein. It is recognized that in addition to human protein targets for various environmental agents, animal protein targets, plant protein targets, Contacting the Sample with the Test Agent(s).

The sample comprising e.g. a cell or tissue lysate, in vitro translated proteins, recombinant proteins, etc. is contacted with one or more test agent(s) to identify proteins bound by or that interact with the test agent(s). In various embodiments the test agent is a human or veterinary pharmaceutical. In various embodiments the test agent is a pharmaceutical listed in the Merck Index 14th Edition. In certain embodiments the test agent is selected from the group consisting of a metabolite, a herbal or other plant extract, a food component, a food additive, an agricultural pesticide or herbicide, a preservative, a colorant, a fragrance, an environmental agent, and a nanoparticle.

Whole Cell Lysate.

The cells, cell line, or tissue sample is typically selected to be one that contains one or more targets for the drug or other test agent, of interest. As a starting point, the cell(s)/sample is treated with a starting drug/test agent concentration ranging from about 10× to 10,000×, preferably from about 100× to about 1,000× the $IC_{50}$ for the drug's biological effect if known. In various embodiments the cells can be treated with this concentration for a short time (e.g., from about 1 min, 15 min, or 30 min to about 1 hr, about 2 hr, about 3 hr, about 5 hr, about ½ day, about 1 day up to about a week).

In certain embodiments whole cell lysate can be obtained, split into two or more equal samples, and then each lysate sample incubated with drug or control (e.g. DMSO or other vehicle of choice). In certain embodiments samples are kept at 4° C. or on ice during the entire procedure except during the proteolysis if possible. Additionally, the enzyme aliquot should be thawed slowly on ice immediately before use and kept on ice until added to the sample. If the enzyme is too concentrated for the experiment it can be diluted to an appropriate concentration (e.g., in ice cold 1×TNC) and preferably immediately used.

In certain embodiments when treating cells with the test agent(s) the cells are grown to an appropriate density and split into equivalent samples. They are then treated with the test agent(s) (e.g., drug(s)) or control/vehicle for the chosen time.

The cells are lysed by any convenient method including, but not limited to lowered ionic strength buffer, surfactant, enzymatic methods (using, e.g., lysozyme, lysostaphin, zymolase, cellulase, mutanolysin, glycanases, proteases, mannase etc.), bead methods (agitating in the presence of e.g., small glass, ceramic, zirconium, or steel beads), sonication, detergent methods (using, e.g., ionic or zwitterionic detergents), solvent extraction, high shear methods (using, e.g., rotor-stator disruptors, valve-type processors, fixed-geometry processors and fixed orifice and constant pressure processors), and the like. It is noted that lysis using M-PER® mammalian protein extraction reagent (Thermo Scientific, Rockford Ill.) with protease and phosphatase inhibitors (to ensure protein integrity and inhibit all endogenous proteases;

these will not significantly affect exogenous proteases) has worked well, but the methods are not so limited.

The protein concentration is measured or an $OD_{280}$ or other measure is performed to set the sample concentrations between test and control equal.

Exact protein concentration is better measure to facilitate the use of a precise exact enzyme:substrate ratio). To make the samples and/or controls equenvalent the volumes are adjusted according to standard methods know to those of skill in the art (e.g., by adding cold lysis buffer to more concentrated samples). Then cold 10×TNC or other appropriate buffer is added to each sample to final 1× and mixed. The proteolysis protocol (see below) is then performed.

In certain embodiments when a lysate is treated with the test agent(s) (e.g., drug(s)), the cells are grown to an appropriate density and lysed using a method, e.g. as described above. In certain embodiments protease and/or phosphatase inhibitors are used and the lysate is kept cold (e.g., 4° C. or on ice at all times). Protein concentration can be measured to facilitate the use of an exact enzyme:substrate ratio. Chilled 10×TNC or other buffer is added to final 1× the solution is mixed well. The lysate is split into equivalent samples and the test agent(s) are added to the chosen final concentration(s). In certain embodiments at least one control sample contain the equivalent amount of DMSO or other vehicle. Dose curves can be used, but in certain preferred embodiments, the final vehicle concentration be the same in each sample. In certain embodiments keep final vehicle concentration at 1% or less if possible. In the case of DMSO, excess DMSO will partially inhibit protease activity, which is why it is desirable to use the same DMSO concentration in each sample of a dose curve). The samples are incubated with the drug on ice or rotated 4° C. for the desired amount of time (e.g., 1, 5, 10, 15, or 30 minutes to overnight or longer. Most test agents/drugs can bind at 4° C. but some may require a short incubation at room temperature. The proteolysis protocol (see below) is then performed.

Recombinant Proteins

In certain embodiments DARTS may be performed on samples containing one, a few, or many (e.g., 1, 2 or more, 5 or more, 10 or more, 20 or more 50 or more, or 100 or more) recombinant proteins to determine direct binding. Concentrations can be determined according to routine methods. It is noted that using at least 100 ng of each recombinant protein per sample for silver staining or 300-400 ng of each for coomassie staining has worked well. In certain embodiments the recombinant proteins are kept on ice except during proteolysis and thawed immediately before use. In certain embodiments large amounts of recombinant proteins are be thawed once, aliquoted, and re-frozen to avoid repeated freeze-thaw cycles that compromise protein integrity. The stock recombinant protein is diluted with 10×TNC or other appropriate buffer and distilled $H_2O$ to the desired volume and 1× final and mixed well. Numerous other buffers can be used if they are preferred for the protein of interest. However, if thermolysin will be used the buffer must contain 10 mM $CaCl_2$. The sample is split into the desired number of equal samples and the test agent(s) are added to the desired concentration. In certain embodiments a control sample should contain the same volume of DMSO or other vehicle. As indicated above, In certain embodiments dose curves should all contain the same final concentration of DMSO because excess DMSO inhibits protease activity. The samples are incubated with the drug on ice or rotated 4° C. for the desired amount of time (e.g., 1, 5, 10, 15, or 30 minutes to overnight or longer. Most test agents/drugs can bind at 4° C. but some may require a short incubation at room temperature. The proteolysis protocol (see below) is then performed.

In Vitro Translated Proteins.

In certain embodiments the sample comprises one or more proteins expressed in an in vitro translation system. Cell free cell-free translation systems are in wide use for in vitro protein synthesis.

The most frequently used cell-free translation systems consist of extracts from rabbit reticulocytes, wheat germ and *Escherichia coli*. These are typically prepared as crude extracts containing the macromolecular components (e.g., 70S or 80S ribosomes, tRNAs, aminoacyl-tRNA synthetases, initiation, elongation and termination factors, etc.) required for translation of exogenous RNA. To ensure efficient translation, each extract can be supplemented with amino acids, energy sources (ATP, GTP), energy regenerating systems (creatine phosphate and creatine phosphokinase for eukaryotic systems, and phosphoenol pyruvate and pyruvate kinase for the *E. coli* lysate), and other co-factors ($Mg^{2+}$, $K^+$, etc.). Two approaches to in vitro protein synthesis are based on the starting genetic material: RNA or DNA. Standard translation systems, such as reticulocyte lysates and wheat germ extracts, typically use RNA as a template; whereas "coupled" and "linked" systems typically start with DNA templates that are transcribed into RNA and then translated.

Rabbit Reticulocyte Lysate

Rabbit reticulocyte lysate is a highly efficient in vitro eukaryotic protein synthesis system used for translation of exogenous RNAs (either natural or generated in vitro). In vivo, reticulocytes are highly specialized cells primarily responsible for the synthesis of hemoglobin, which represents more than 90% of the protein made in the reticulocyte. These immature red cells have already lost their nuclei, but contain adequate mRNA, as well as complete translation machinery, for extensive globin synthesis. The endogenous globin mRNA can be eliminated by incubation with $Ca^{2+}$-dependent micrococcal nuclease, which is later inactivated by chelation of the $Ca^{2+}$ by EGTA. A nuclease-treated reticulocyte lysate is commercially available from Ambion/Applied Biosystems (Foster City, Calif.). Rabbit reticulocyte lysates have low nuclease activity and are capable of synthesizing a large amount of full-length product. It is noted that in the examples provided herein, IVT was performed using Promega TnT T7 Quick Coupled Transcription/Translation.

Wheat Germ Extract

In certain embodiments wheat germ extract is a convenient alternative to the rabbit reticulocyte lysate cell-free system. This extract has low background incorporation due to its low level of endogenous mRNA. Wheat germ lysate efficiently translates exogenous RNA from a variety of different organisms, from viruses and yeast to higher plants and mammals. The wheat germ extract is recommended for translation of RNA containing small fragments of double-stranded RNA or oxidized thiols, which are inhibitory to the rabbit reticulocyte lysate. Both reticulocyte and wheat germ extracts translate RNA isolated from cells and tissue or those generated by in vitro transcription. When using RNA synthesized in vitro, the presence of a 5' cap structure may enhance translational activity. Typically, translation by wheat germ extracts is more cap-dependent than translation by reticulocyte extracts. If capping of the RNA is impossible and the protein yield from an uncapped mRNA is low, the coding sequence can be subcloned into a prokaryotic vector and expressed directly from a DNA template in an *E. coli* cell-free system.

*E. coli* Cell-Free System

*E. coli* cell-free systems consist of a crude extract that is rich in endogenous mRNA. The extract is incubated during preparation so that this endogenous mRNA is translated and subsequently degraded. Because the levels of endogenous mRNA in the prepared lysate are low, the exogenous product is easily identified. In comparison to eukaryotic systems, the E. coli extract has a relatively simple translational apparatus with less complicated control at the initiation level, allowing this system to be very efficient in protein synthesis. Bacterial extracts are often unsuitable for translation of RNA, because exogenous RNA is rapidly degraded by endogenous nucleases. There are some viral mRNAs (TMV, STNV, and MS2) that translate efficiently, because they are somewhat resistant to nuclease activity and contain stable secondary structure. However, E. coli extracts are good for coupled transcription:translation from DNA templates.

"Linked" and "Coupled" Transcription:Translation Systems

In standard translation reactions, purified RNA is used as a template for translation. "Linked" and "coupled" systems, however, use DNA as a template. RNA is transcribed from the DNA and subsequently translated without any purification. Such systems typically combine a prokaryotic phage RNA polymerase and promoter (e.g., T7, T3, SP6, etc.) with eukaryotic or prokaryotic extracts to synthesize proteins from exogenous DNA templates. DNA templates for transcription:translation reactions may be cloned into plasmid vectors or generated by PCR.

Linked Transcription:Translation

The "linked" system is a two-step reaction, based on transcription with a bacteriophage polymerase followed by translation in the rabbit reticulocyte lysate or wheat germ lysate. Because the transcription and translation reactions are separate, each can be optimized to ensure that both are functioning at their full potential. Many commercially available eukaryotic coupled transcription:translation systems perform both reactions in a single tube.

Coupled Transcription:Translation

Unlike eukaryotic systems where transcription and translation occur sequentially, in E. coli, transcription and translation occur simultaneously within the cell. In vitro E. coli translation systems are thus performed the same way, coupled, in the same tube under the same reaction conditions. During transcription, the 5' end of the RNA becomes available for ribosomal binding and undergoes translation while its 3' end is still being transcribed. This early binding of ribosomes to the RNA maintains transcript stability and promotes efficient translation. This bacterial translation system gives efficient expression of either prokaryotic or eukaryotic gene products in a short amount of time. In certain embodiments to improve protein yield and initiation fidelity, the DNA template has a Shine-Dalgarno ribosome binding site upstream of the initiator codon. Capping of eukaryotic RNA is not required. Use of E. coli extract can also eliminate cross-reactivity or other problems associated with endogenous proteins in eukaryotic lysates. The E. coli S30 extract system allows expression from DNA vectors containing natural E. coli promoter sequences (such as lac or tac).

In various embodiments the In vitro translated protein mixture is split into equivalent samples and the test agent(s) are added to the chosen final concentration(s). In certain embodiments at least one control sample contains the equivalent amount of DMSO or other vehicle. Dose curves can be used, but in certain preferred embodiments, the final vehicle concentration be the same in each sample. In certain embodiments the final vehicle concentration is kept at 1% or less if possible. In the case of DMSO, excess DMSO will partially inhibit protease activity, which is why it is desirable to use the same DMSO concentration in each sample of a dose curve).

The samples are incubated with the drug on ice or rotated 4° C. for the desired amount of time (e.g., 1, 5, 10, 15, or 30 minutes to overnight or longer. Most test agents/drugs can bind at 4° C. but some may require a short incubation at room temperature. The proteolysis protocol (see below) is then performed.

Proteolysis.

Proteolysis can be accomplished using any suitable method. In certain embodiments one or more proteases are used. Suitable proteases include one or more proteases such as serine proteases, threonine proteases, cysteine proteases, aspartate proteases, metalloproteases, glutamic acid proteases, and the like. In certain embodiments illustrative embodiments, proteolysis is performed using subtilisin (a serine endopeptidase), and/or thermolysin (a metalloprotease), and/or Proteinase K, and/or trypsin, and/or chymotrypsin, and/or pronase. These proteases are intended to be illustrative and not limiting. Using the teachings provided herein other proteases and/or combinations of proteases will be available to one of skill in the art.

In certain embodiments in a single target identification experiment, digestion conditions for each sample and/or sample(s) and control(s) should be identical. The ideal enzyme:substrate ratio and digestion time will vary for each protein and under different conditions and can be optimized using routine methods. One useful starting point using thermolysin as the protease is to begin with an enzyme:substrate ratio of 1:20 (wt/wt) and digestions of 5 and 30 minutes. For subtilisin, an enzyme:substrate ratio of 1:1000 (wt/wt) and digestions of 10 minutes and 1 hour provide good starting points. If these values results in over- or under-digestion of the sample, subsequent protocols can modify the enzyme:substrate ratio by about 2 fold or about 5 fold to about 10 fold or 20 fold, and/or the digestion time can be modified for finer proteolysis adjustments.

In one illustrative embodiment, digestion is begun by removing the sample(s) from ice, adding stock enzyme to appropriate final ratio, quickly mixing the sample, e.g., by pipetting and/or flicking tube, centrifuging the sample (e.g., in a microfuge) to bring contents to bottom of the tube, and incubating at room temperature. To stop digestion with thermolysin, EDTA can be added to a final 20 mM, mixing the sample and placing the sample on ice immediately. To stop digestion with subtilisin, concentrated SDS-PAGE loading buffer can be added to final 1×, the sample mixed well, and immediately boiling the sample.

The foregoing is illustrative and not limiting. Methods of initiating and stopping digestions with other proteases or protease combinations will be known to those of skill in the art.

Detection.

The detection, identification, and/or quantification of a protein or protein fragment that is protected from proteolysis by binding or interaction with a test agent in the methods described herein can be accomplished using methods of protein detection/quantification well known to those of skill in the art. Such methods include, for example, 1D and 2-D electrophoresis, capillary electrophoresis, microfluidics analysis systems (lab-on-a chip), chromatography, HPLC, western blot, mass spectroscopy, and the like.

In certain illustrative embodiments, initial analysis of protein abundance changes is performed by separating the samples post-proteolysis with 1D or 2D SDS-PAGE gels and staining (e.g., with silver, coomassie blue, or sypro). Any bands that appear enriched or depleted in the drug-containing sample after proteolysis are then cut out for subsequent protein identification and quantification by mass spectrometry.

In certain embodiments the limitation of DARTS when using cell or tissue lysates is the detection of very low abundant proteins by gel staining and mass spectrometry. This limitation can be circumvented by the use of protocols that do not require protein abundance differences to be visible on a stained gel. For example, in one approach, larger protein samples are proteolysed, followed by removal of digested peptides and amino acids and concentration of the remaining proteins. These samples are then directly analyzed by nanoLC-MS/MS without prior gel separation and small protein abundance differences identified through differential analysis of spectral counts and chromatograph profiles. The initial MS/MS/data can be collected using data dependent acquisition and dynamic exclusion providing the best opportunity to obtain sufficient spectral data to identify the greatest number of proteins in the sample run. However, if insufficient data is collected in the first MS run to identify any significantly changing proteins in the sample, targeted analysis of these specific peptides can be performed in subsequent MS runs to provide the maximum information possible to positively identify the target proteins.

As shown in the Examples provided herein, DARTS has been demonstrated to work in a number of different systems. For example, DARTS has been tested using purified, recombinant protein. Specifically, DARTS was used successfully to show that binding of Rapamycin or FK506 to their initial intracellular target FKBP12 provided protection against subtilisin digestion; this is specific because under identical conditions, Wortmannin, which does not bind FKBP12, did not change its proteolytic susceptibility in comparison to DMSO alone. DARTS has also been shown effective with proteins generated using in vitro transcription and translation (IVT) using the rabbit reticulocyte lysate system. A biotinylated IVT-generated mTOR C-terminal fragment containing the FKBP12-rapamycin binding domain was protected from digestion with thermolysin when incubated with FKBP12 and rapamycin, but not by either one alone. Specificity of this technique was further shown by the fact that an identical mTOR fragment containing the S2035T mutation, which is unable to bind the FKBP12-rapamycin complex, was not protected from thermolysin digestion. DARTS has also been demonstrated to be effective using whole cell lysates. This was shown by performing DARTS on lysates of Jurkat cells treated with the anti-cancer natural product Didemnin B or DMSO. Analysis identified EF1a to be the primary protein enriched in the DB sample in a dose-dependent manner.

Finally, DARTS was used to reveal the molecular target of resveratrol, an anti-aging natural product from red grapes and wine. Since DARTS combines the advantages of currently available affinity-based and affinity-free methods, while at the same time lacking many of their limitations, it is believed to represent the single most versatile and comprehensive target ID method developed to date.

The examples and methods described herein are intended to be illustrative and not limiting. Using the teaching provided herein, other variations of the illustrated protocols will be available to one of skill in the art.

EXAMPLES

The following examples are offered to illustrate, but not to limit the claimed invention.

Example 1

Target Identification Using Drug Affinity Responsive Target Stability (DARTS)

Identifying the molecular targets for the beneficial or detrimental effects of small molecule drugs is an important and currently unmet challenge. We have developed a method, drug affinity responsive target stability (DARTS) that takes advantage of a reduction in the protease susceptibility of the target protein upon drug binding. DARTS is universally applicable because it requires no modification of the drug and is independent of the mechanism of drug action. We demonstrate use of DARTS to identify known small-molecule-protein interactions and to reveal the eukaryotic translation initiation machinery as a molecular target for the longevity-enhancing plant natural product resveratrol. We envisage that DARTS will also be useful in global mapping of protein-metabolite interaction networks and in label-free screening of unlimited varieties of compounds for development as molecular imaging agents.

We sought to develop a simple, universally applicable target identification approach that analyzes direct drug binding to targets. We hypothesized that a protein might become less susceptible to proteolysis when it is drug-bound than when it is drug-free and that this phenomenon could be exploited for target identification. This would allow the protein target of a drug to be revealed, without requiring modification or immobilization of the small molecule. Because our method, termed DARTS (drug affinity responsive target stability), is not limited by synthetic chemistry and is independent of any biological effects of the drug (save its binding to the target protein), it can potentially be used to identify the target for any small molecule.

DARTS Strategy and Proof-of-Concept.

Figure 2A:
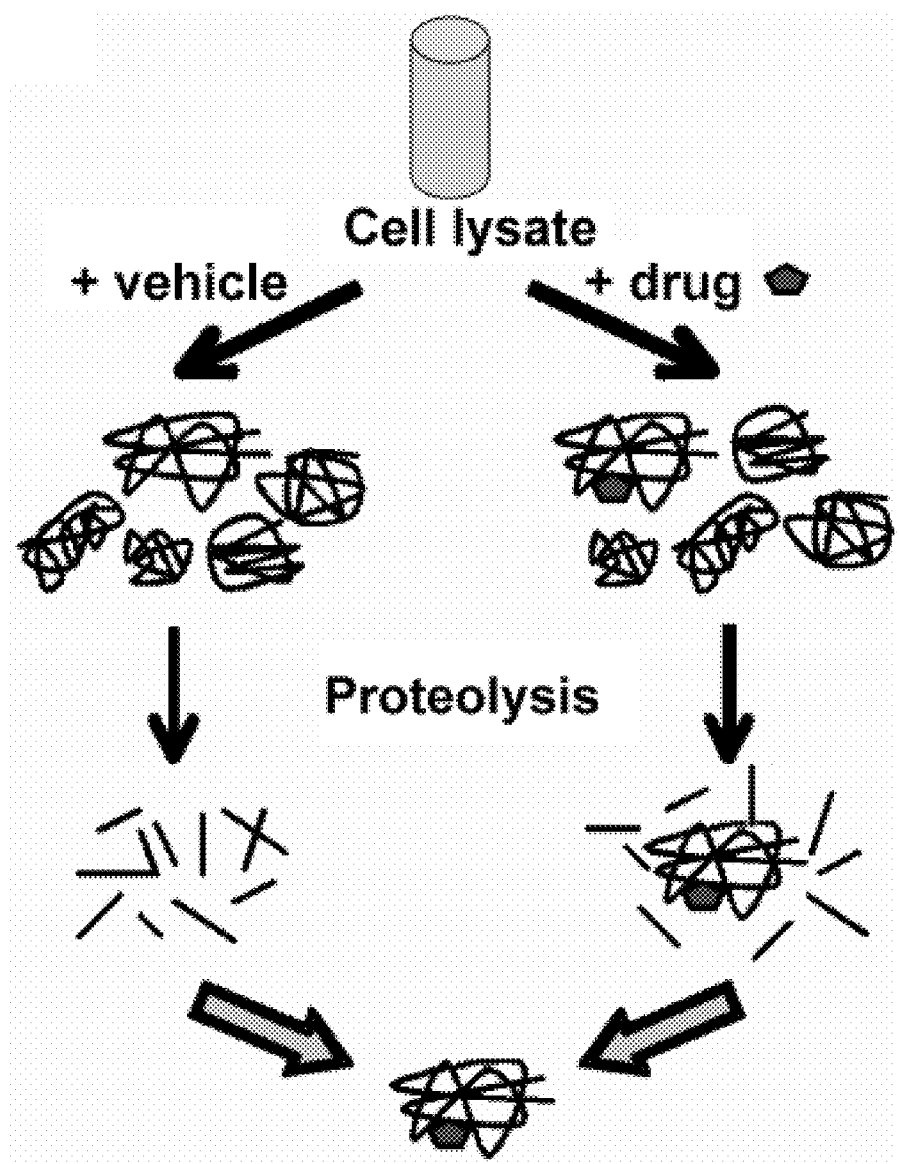
FIGS. 2A, 2B, and 2C illustrate an embodiment of the DARTS method for drug target identification.

One illustrative basic strategy of DARTS is shown in FIG. 2A. Binding of drugs is proposed to stabilize target proteins, either globally or locally, e.g., in a specific conformation or by simply masking protease recognition sites, thereby reducing protease sensitivity of the target protein. Prior to our studies, it was unclear whether protease susceptibility of the target protein would be different in the absence of large conformational changes, e.g., upon binding of small hydrophobic drugs. Another question was whether the strategy would be amenable to lower-affinity ligands, e.g., clinically used drugs, which encompass a wide range of binding affinities, and hits identified from chemical genetic screens, which typically are in the micromolar range.

Figure 2B:
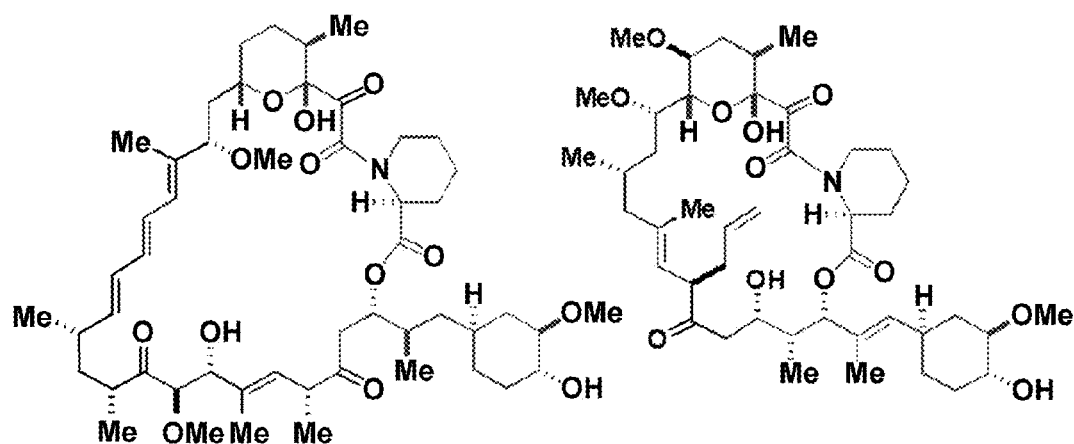
Figure 2B:
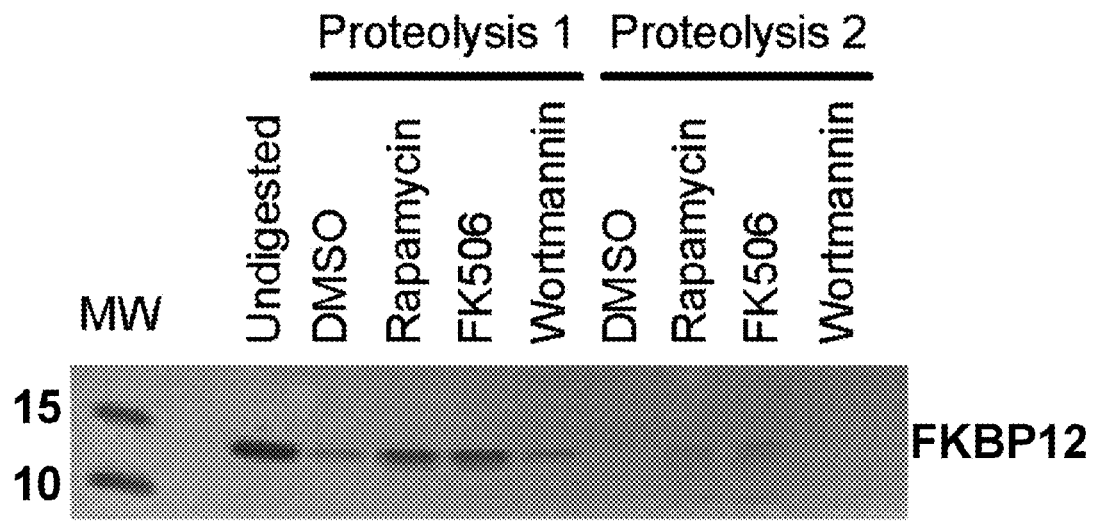
Figure 6A:
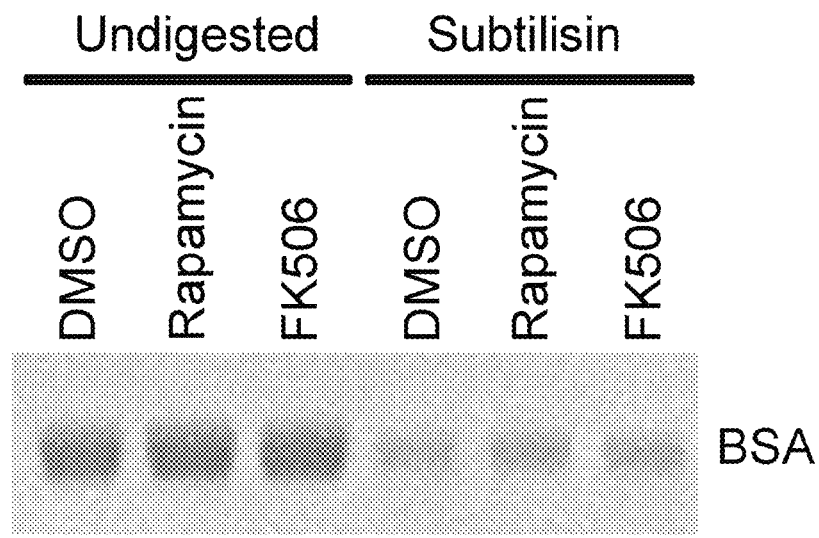
FIG. 6A: Subtilisin activity is unaffected by the small molecules used for FIG. 1B under identical experimental conditions except with BSA as a non-binder control.

As a proof-of-principle, we examined the well-studied immunophilin FKBP12, which is the target for the nanomolar immunosuppressant drugs rapamycin and FK506 (Van Duyne et al. (1993) *J Mol Biol* 229: 105-124). Proteolysis of FKBP12 by the protease subtilisin was clearly decreased by the presence of rapamycin or FK506 (FIG. 2B). This protection is selective: incubation with wortmannin, a drug that does not bind FKBP12, did not prevent proteolysis (FIG. 2B), and the drugs had no effect on subtilisin activity (FIG. 6A). Since X-ray co-crystal structures showed that binding of FK506 or rapamycin does not cause a conformational change in FKBP12 (Id.), our results above suggest that drug binding alone is likely sufficient to stabilize the bound protein in the protease-resistant state. This result could be due to a direct change in the protein folding-unfolding equilibrium upon ligand binding (Park and Marqusee (2005) *Nat Methods* 2: 207-212).

Figure 2C:
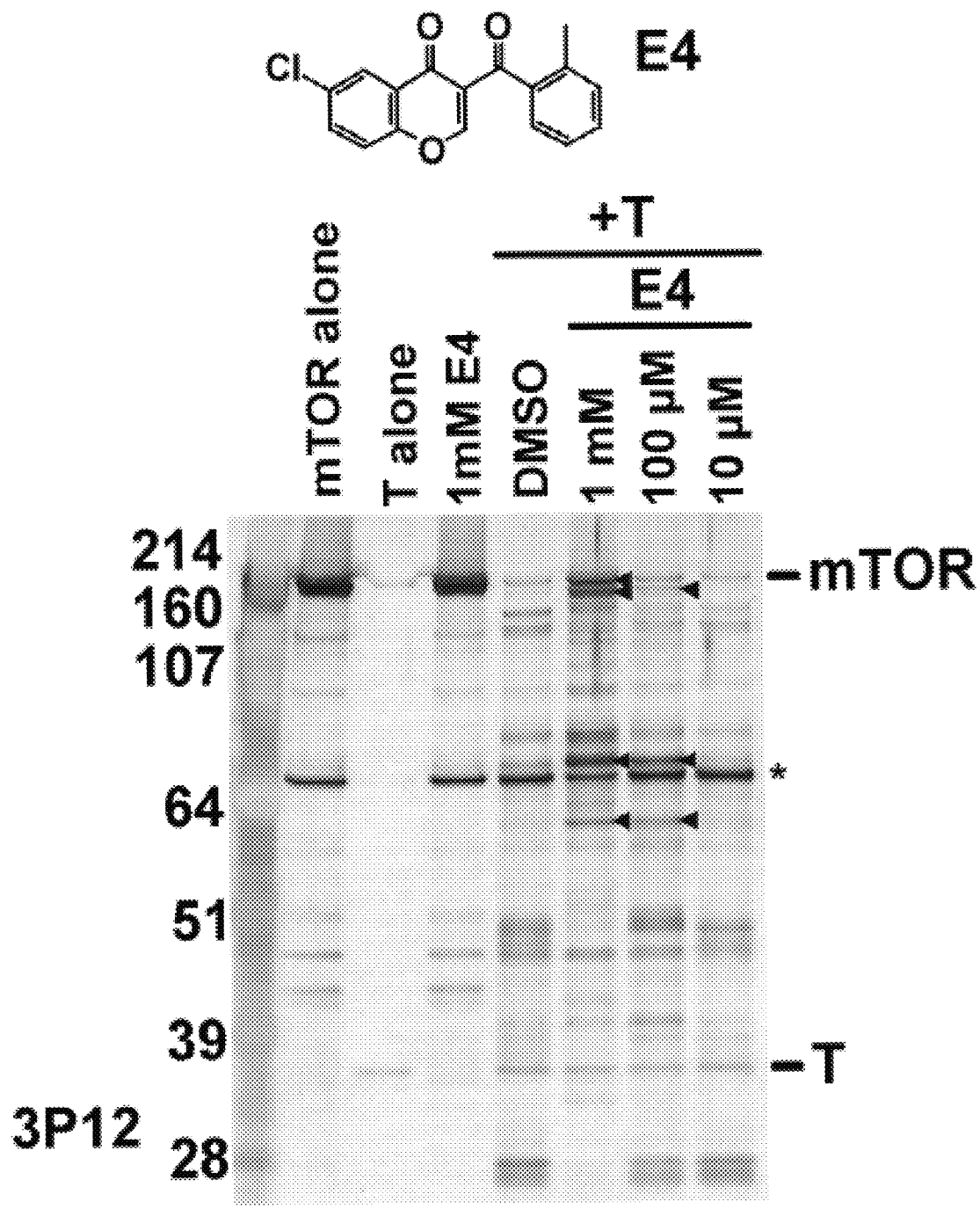
Figure 6B:
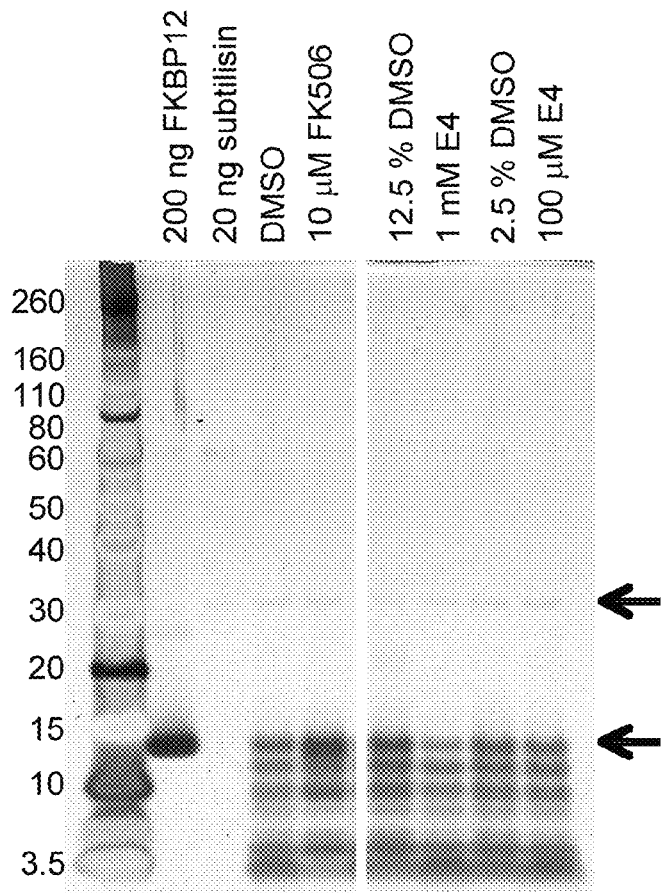
FIG. 6B: E4 does not confer proteolysis protection on FKBP12, a control protein that does not bind to the small molecule. 200 ng of C-terminal $His_6$-tagged human FKBP12 was incubated with E4, FK506 (positive control), or DMSO (solvent control) for 2 hr at 4° C., followed by digestion with 20 ng subtilisin Carlsberg for 30 min at room temperature. Samples were run on NUPAGE® Novex 4-12% Bis-Tris gel (Invitrogen) and silver-stained. Samples above were all run on the same gel.

Given that rapamycin and FK506 are among the most potent and specific drugs available, we decided to test if DARTS would work similarly with a much weaker inhibitor. E4 is a mid-micromolar kinase inhibitor of mTOR identified from a phenotype-based chemical genetic screen. Indeed, proteolysis of mTOR by thermolysin was decreased by E4 in a dose-dependent manner (FIG. 2C and FIG. 6B).

DARTS Using Complex Protein Mixtures.

The experiments above established that DARTS can efficiently test, screen, or verify drug-protein interactions when the protein is available in relatively pure form. For DARTS to be generally useful as a discovery tool, however, applicability to complex protein mixtures (such as cell lysates) would be desirable. To demonstrate feasibility, we performed DARTS using human Jurkat cells treated with didemnin B (DB), an anti-cancer marine natural product whose binding to EF-1 alpha had previously been well-characterized (Crews et al. (1994) *J Biol Chem* 269: 15411-15414). Given that EF-1 alpha is a highly abundant protein, we first tested whether in the DARTS protocol DB would protect EF-1 alpha from proteolysis and result in a detectable difference. Indeed, DARTS revealed a strong protected band at ~50 kDa in the proteolysed extracts of DB-treated cells (FIG. 3A), whereas no detectable difference was observed in the same samples that underwent mock digestion.

Figure 3A:
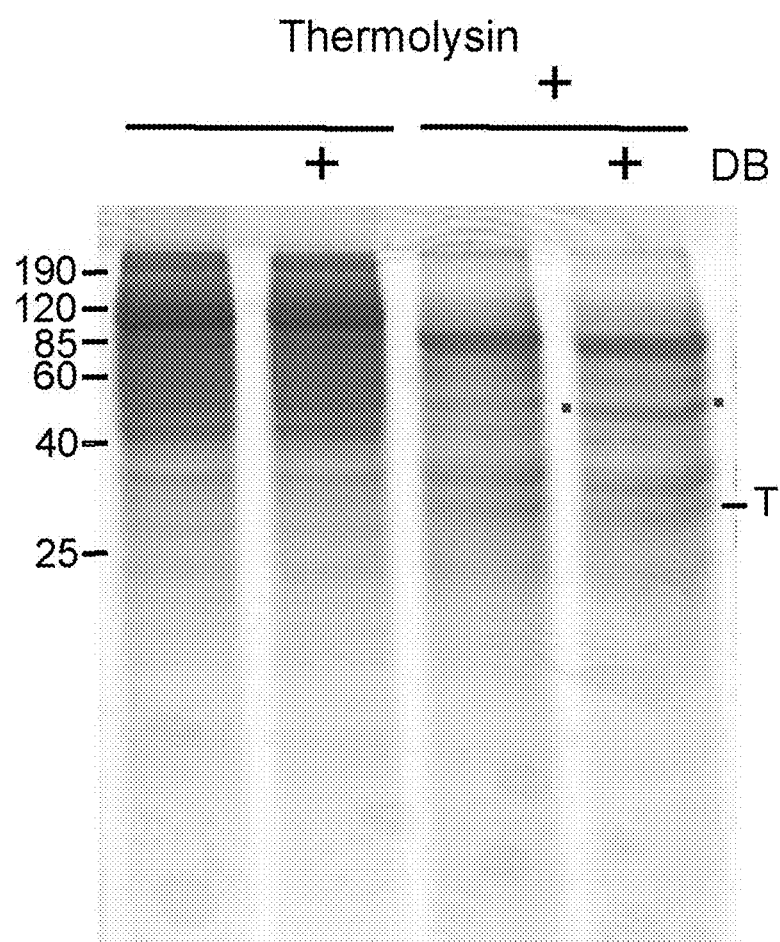
FIGS. 3A, 3B, and 3C, illustrate DARTS using whole cell lysate.
Figure 3B:
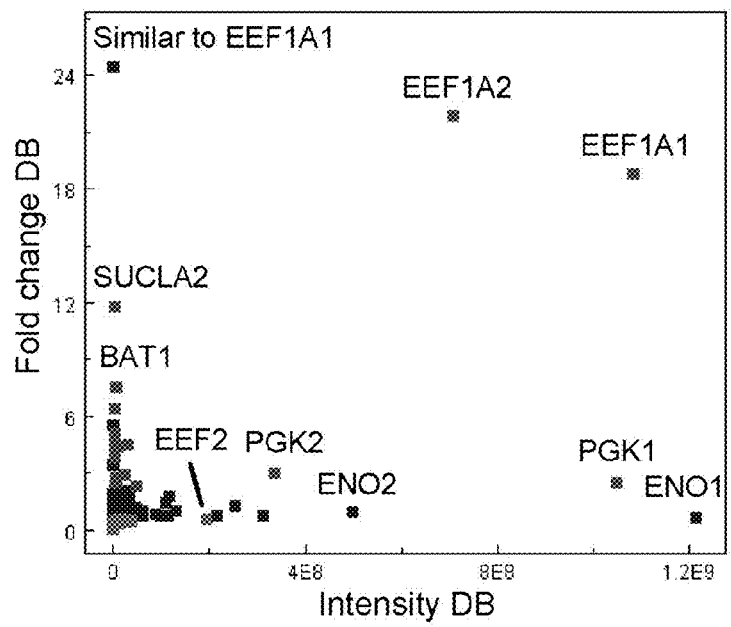
Figure 7:
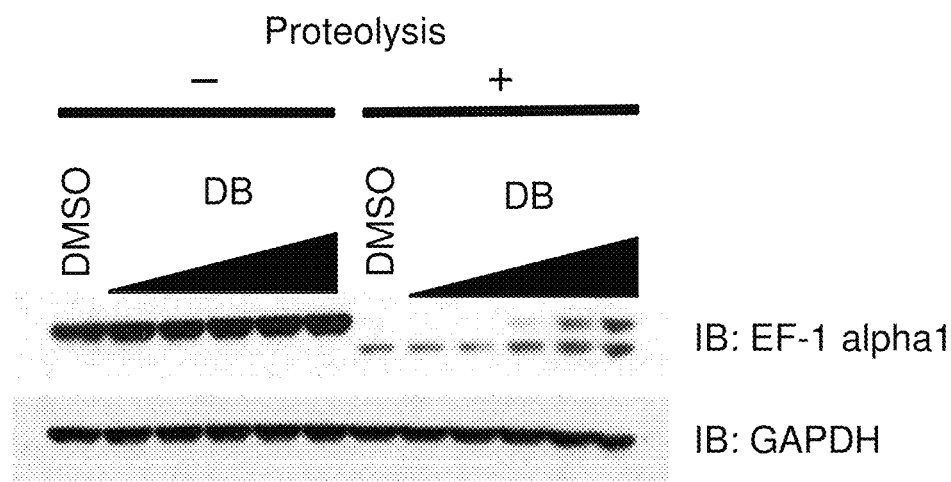
FIG. 7 illustrates DARTS with Didemnin B using whole-cell lysates. Lysates from untreated human Jurkat cells were incubated with DMSO control or DB (1 ng/mL, 10 ng/mL, 100 ng/mL, 300 ng/mL, and 1 μg/mL) for 30 min at room temperature. Each sample was then split into two, which underwent thermolysin proteolysis, or mock digestion, respectively, followed by western blot analysis. Protection can be seen starting at 100 ng/mL.
Figure 8A:
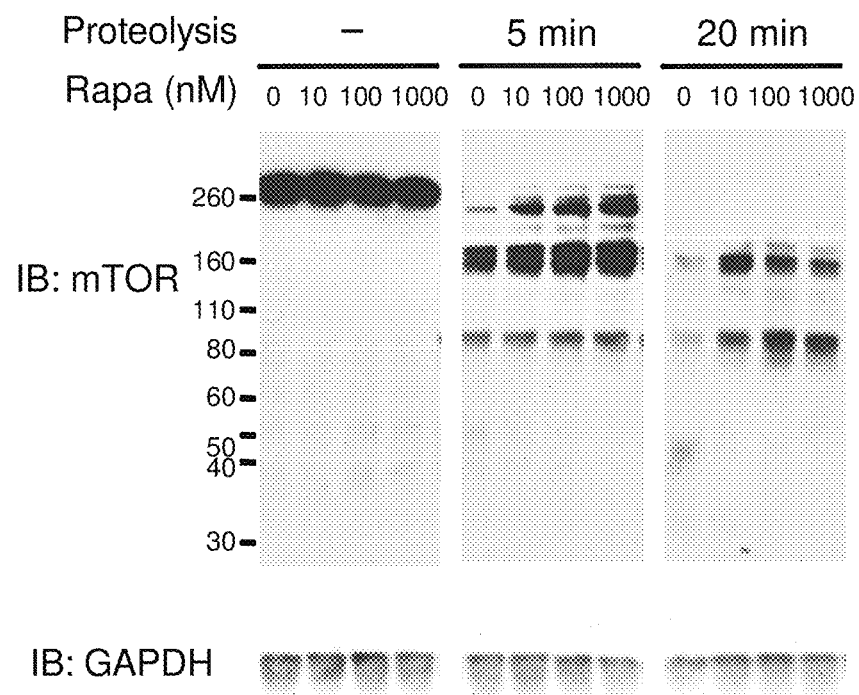
FIG. 8A illustrates DARTS using rapamycin-treated cells. A549 cells were treated with indicated concentrations of rapamycin, or DMSO control, for 30 min and washed in PBS once before lysis in Triton X-100 lysis buffer [50 mM Tris-HCl pH 7.5, 0.5% Triton X-100, 200 mM NaCl, 10% glycerol, 1 mM DTT, Roche protease inhibitor cocktail, and phosphatase inhibitors (10 mM Na-pyrophosphate, 50 mM NaF, and 0.1 mM orthovanadate)]. Protein concentration was determined by BCA Protein Assay kit (Pierce). Fifty-two microgram of cell lysate was used for DARTS experiment in a total of 10 μL. All steps were performed on ice or at 4° C. to help prevent premature protein degradation. Each sample was then quickly warmed to room temperature and immediately proteolysed with 100 ng thermolysin for every 52 μg of lysate for the indicated time. To stop the proteolysis reaction, 1 μL of 0.5 M EDTA (pH 8.0) was added to each sample, mixed well, and immediately placed on ice. After adding SDS sample buffer, samples were subjected to 6% Tris-HCl SDS-PAGE and Western blotted with anti-mTOR polyclonal antibody (Cell Signaling, MA).
Figure 8B:
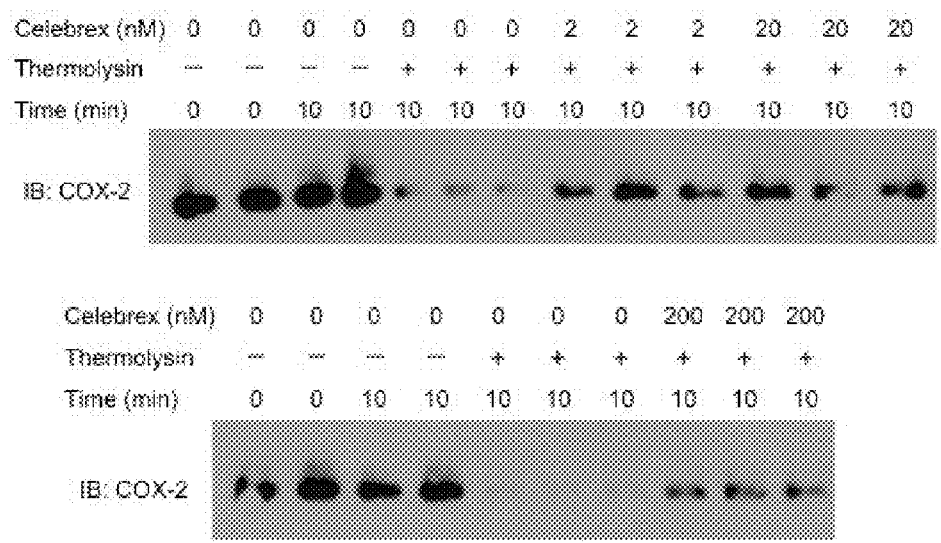
FIG. 8B shows DARTS with celecoxib, using cell lysates. Murine RAW264.7 cells were treated with LPS (200 ng/mL) for 18 hours, to induce COX2 expression. Cells were washed with cold PBS, and lysed with M-PER supplemented with Roche protease inhibitor cocktail and phosphatase inhibitors, according to manufacturer's instructions (Pierce). Protein concentration was determined using the Bradford Protein Assay kit (BIO-RAD). Whole cell lysates were diluted with proteolysis reaction buffer [50 mM Tris-HCl pH 8.0, 50 mM NaCl, 10 mM CaCl22]. All steps were performed on ice, to prevent premature protein degradation. Lysates (24 μg) were incubated with ethyl alcohol vehicle control, or with celecoxib (Panacea Biotec Ltd., New Delhi, India) at concentrations of 2, 20 and 200 nM, for 2 hours at 9° C., in triplicate. Untreated lysates diluted to the same final volume were used as controls. Samples were proteolysed with 1 μg thermolysin (Sigma, #88303) for every 20 μg lysate, at 25° C. for 10 min. To stop the proteolysis the reaction tubes were shifted to 4° C. and EDTA (pH 8.0, 50 mM final concentration) and SDS-PAGE loading buffer were added to each sample. The reaction tubes were then incubated at 100° C. for 10 minutes. Aliquotes of each sample were subjected to electrophoresis on 12% SDS-PAGE. Following electrophoresis, proteins were transferred to PVDF membranes. For Western blotting, anti-COX2 antibody sc-1747-R (Santa Cruz Biotechnology) was used. Thermolysin stocks were stored at −20° C.; new thermolysin stocks were used for each proteolysis experiment. The upper and lower illustrations are separate electrophoresis experiments from samples prepared at the same time. Because electrophoresis, transfer and immunoblotting of the samples treated with 200 nM celecoxib were performed separately from samples treated with 2 and 20 nM celecoxib, untreated extracts and extracts treated with thermolysin in the absence of celecoxib are shown for both gels.

Examination of the protected band and the matching gel region of the control lane by mass spectrometry confirmed that EF-1 alpha was the primary protein present at higher abundance in the DB-treated sample (FIG. 3B). This analysis does not exclude the possibility of other protected targets of lower abundance that were not evident by eye on the gel. DB-concentration dependent proteolytic protection of EF-1 alpha was also observed by immunoblotting, both when intact cells were treated with DB (FIG. 2C) and when the lysates of untreated cells were incubated with DB in vitro (FIG. 7). The generality of this approach is further supported by experiments using diverse protein-drug pairs ranging from nano- to micro-molar: mTOR-rapamycin, COX-2celecoxib, and SCF E3 ubiquitin ligase-inhibitor (FIG. 8). Furthermore, DARTS is not enzyme specific, and much higher overall digestion efficiency can be achieved using other proteases while retaining protection of the target protein (see Example 2 and FIG. 9).

Identification of a New Molecular Target for Resveratrol Using DARTS.

Figure 4A:
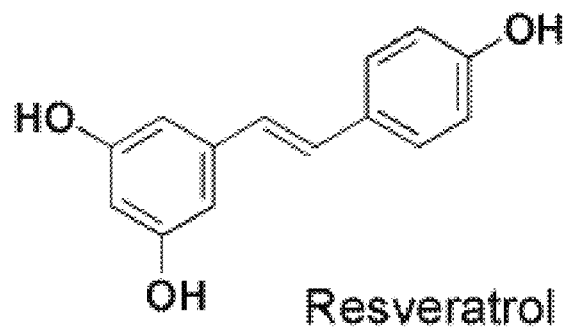
FIGS. 4A-4E show that DARTS identifies a new molecular target of resveratrol.

Next, we applied DARTS to identify a molecular target of resveratrol, a compound in red grapes and wine known for various health benefits including lifespan extension (Wood et al. (2004) *Nature* 430: 686-689). Although resveratrol influences the activities of many proteins, no direct molecular target has been demonstrated. Low specific binding affinity as suspected from its modest size and structure (FIG. 4A), poor potency, and potential requirement for the polyphenol groups for its activity have discouraged generation of affinity reagents for target identification. Also, even at saturating concentrations resveratrol inhibits yeast growth only very weakly if at all, making it a poor candidate for target identification using fitness profiling strategies.

Figure 4B:
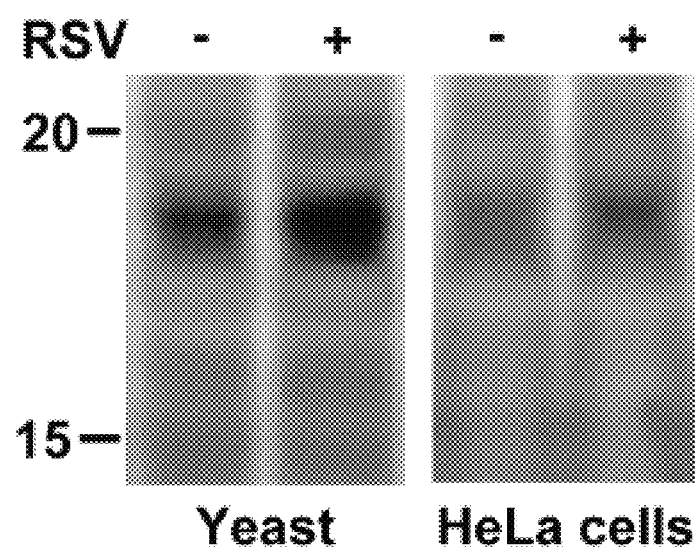
Figure 4C:
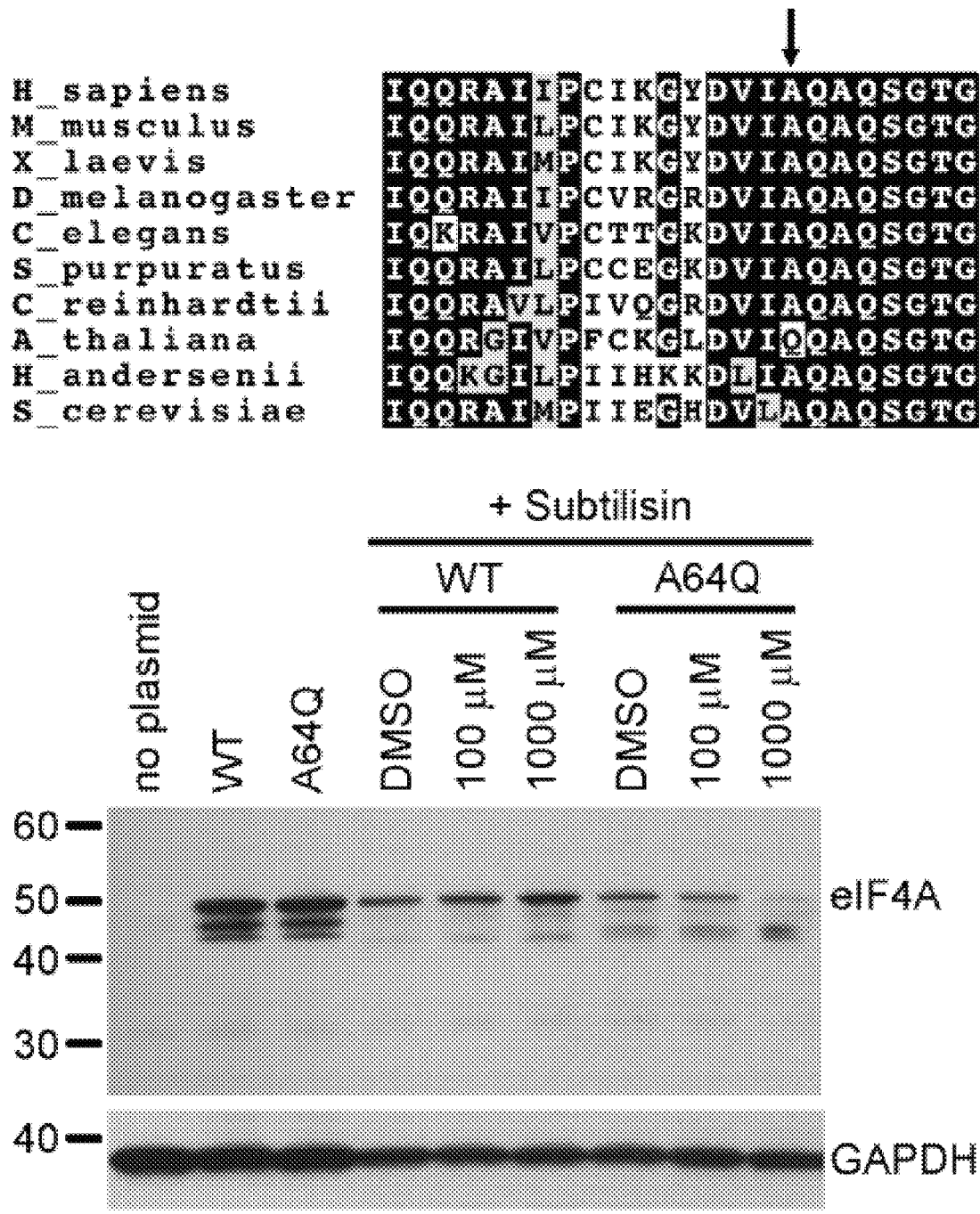
Figure 10:
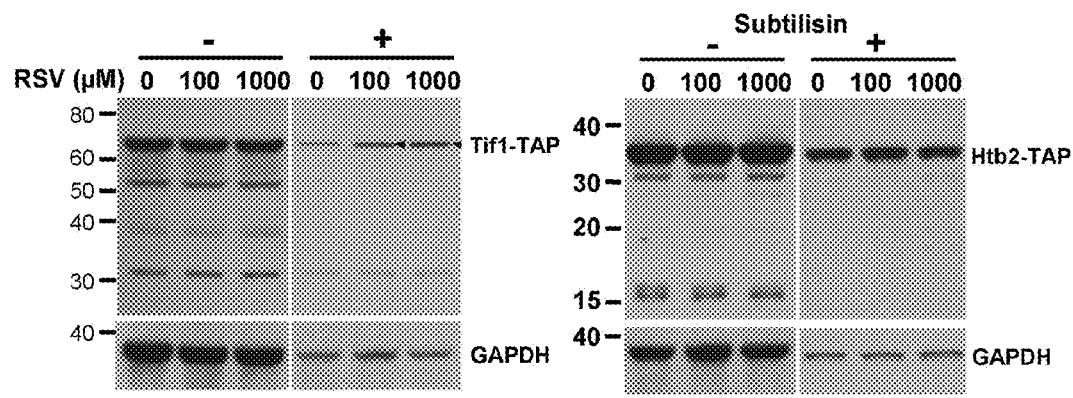
FIG. 10 shows that resveratrol protects the TAP-tagged Tif1, but not an unrelated control Htb2, from proteolysis. Arrow: protein protected from proteolysis.
Figure 11A:
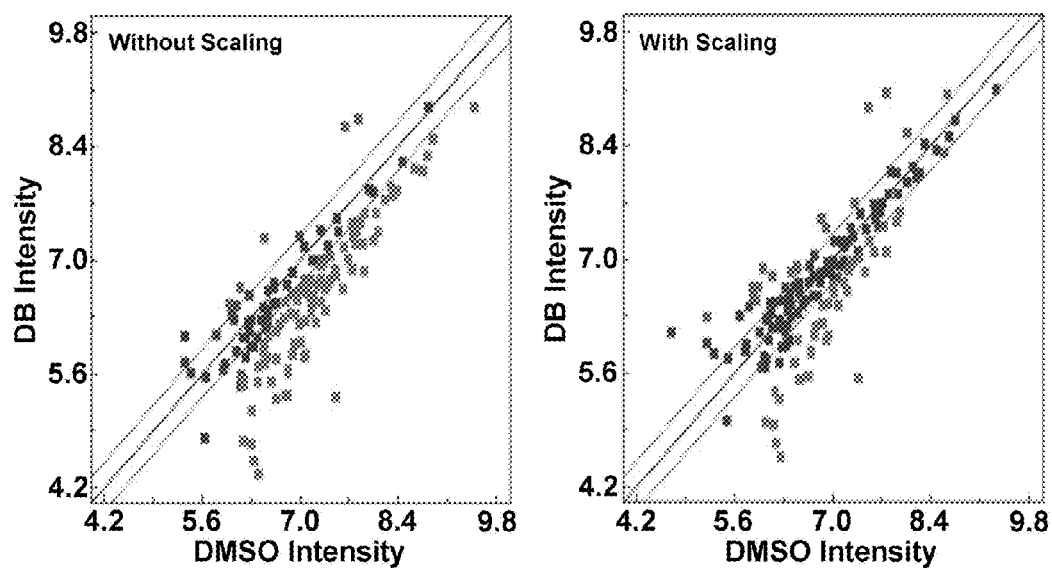
FIG. 11A shows a Comparison of MS data analysis with and without intensity scaling. Protein abundance levels for the protected band from FIG. 2D were compared using Rosetta Elucidator both with and without intensity scaling. X-axis, $\log_{10}$ protein intensity of the DMSO sample; Y-axis, $\log_{10}$ protein intensity of the DB sample. Red dot, protein enriched >2-fold with a p-value <0.001; green dot, protein depleted >2-fold with a p-value <0.001; blue dot, unchanged protein. Blue line, ratio=1; red line, ratio=2.
Figure 11B:
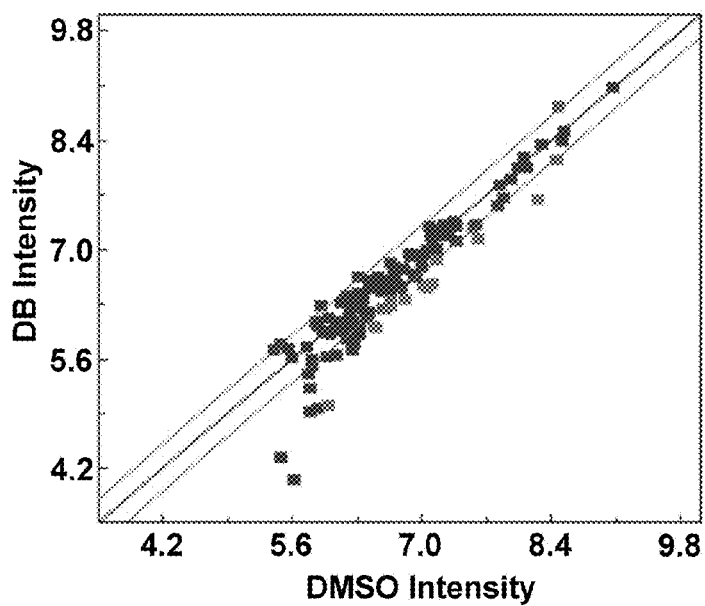
FIG. 11B: MS analysis of a control band. Protein abundance levels were compared for a control band at 35 kDa with no difference in staining intensity between the DB and control samples after proteolysis. Axes and dots are labeled same as in FIG. 11A.
Figure 12:
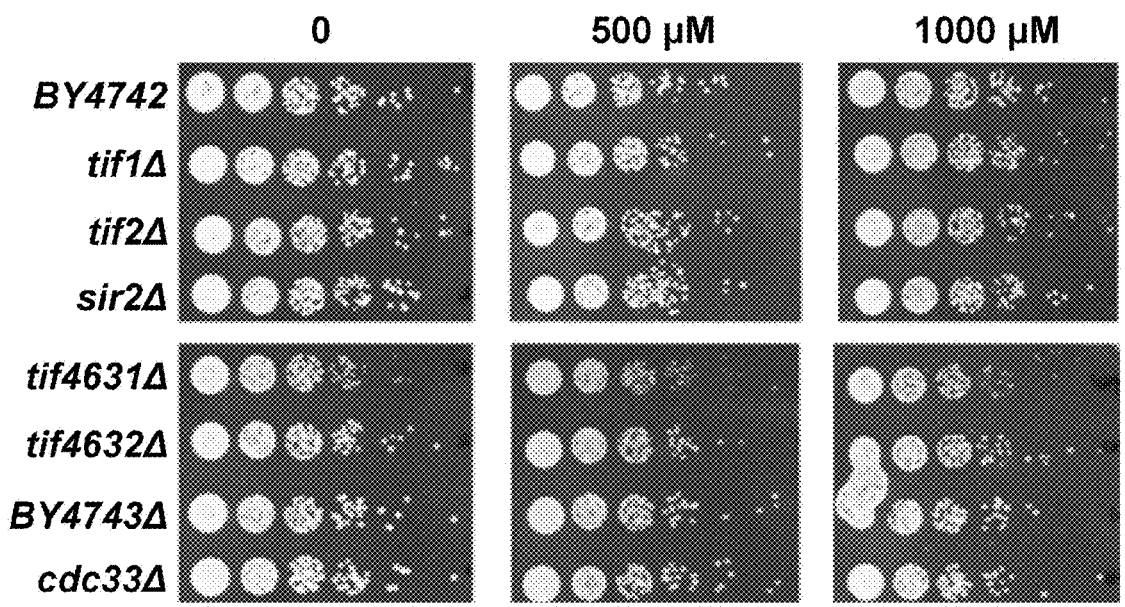
FIG. 12 shows that resveratrol shows no detectable inhibition of yeast cell growth.

DARTS with resveratrol-dosed yeast cell lysates revealed two silver-stained bands between the 15 and 20 kDa MW markers that were more intense in the resveratrol-treated lysate post-proteolysis as compared to vehicle control (FIG. 4B). Mass spectrometry analysis of both bands showed that eIF4A, along with several ribosomal proteins, were enriched in the resveratrol-treated sample (see, e.g., Table 1). This enrichment was confirmed by western blotting using the TAP-tagged (Ghaemmaghami et al. (2003) *Nature* 425: 737-741) eIF4A yeast strain (FIG. 10). This finding suggests that resveratrol might directly bind to one or more proteins comprising the protein translation machinery. Potential direct binding was further supported by a target mutation analysis, where a Tif1 A64Q point mutant confers resistance to resveratrol (FIG. 4C). While the alanine is conserved throughout fungi and animals, plants have a glutamine at this position and the bulkier side chain is hypothesized to protect plant eIF4A from resveratrol inhibition by minimizing self binding.

TABLE 1

Enriched proteins in the resveratrol DARTS sample.

| Protein | Fold Change | P-value | Accession Number | Band |
|---|---|---|---|---|
| 60S ribosomal protein L26-B | 11.107 | 1.35E−04 | P53221 | Lower |
| 60S ribosomal protein L26-A | 9.181 | 8.12E−27 | P05743 | Lower |
| 60S ribosomal protein L24 | 6.05 | 1.24E−07 | P04449, P24000 | Upper |
| 40S ribosomal protein S23 | 4.84 | 1.05E−04 | P32827 | Upper |
| 40S ribosomal protein S26 | 4.701 | 0.002 | P39938, P39939 | Upper |
| 60S ribosomal protein L35 | 3.774 | 7.27E−18 | P39741 | Lower |
| 40S ribosomal protein S15 | 3.677 | 5.53E−06 | Q01855 | Lower |
| 60S ribosomal protein L25 | 3.564 | 3.45E−21 | P04456 | Lower |
| Histone H2A | 3.002 | 3.19E−04 | P04911, P04912 | Lower |
| 40S ribosomal protein S16 | 2.906 | 2.17E−19 | P40213 | Lower |
| 60S ribosomal protein L21-A | 2.777 | 0.007 | Q02753 | Upper |
| 60S ribosomal protein L25 | 2.713 | 9.60E−05 | P04456 | Upper |
| 60S ribosomal protein L27-A | 2.554 | 2.37E−04 | P0C2H6, P0C2H7 | Upper |
| Ornithine aminotransferase | 2.531 | 9.05E−04 | P07991 | Lower |
| 40S ribosomal protein S26-B | 2.429 | 4.32E−10 | P39938, P39939 | Lower |
| 40S ribosomal protein S18 | 2.412 | 7.16E−06 | P35271 | Lower |
| 60S ribosomal protein L34 | 2.383 | 1.89E−06 | P40525, P87262 | Lower |
| Histone H2B | 2.229 | 5.42E−04 | P02293, P02294 | Lower |
| 40S ribosomal protein S12 | 2.07 | 5.42E−04 | P48589 | Lower |
| 40S ribosomal protein S19 | 1.965 | 3.62E−08 | P07280, P07281 | Lower |
| ATP-dependent RNA helicase eIF4A | 1.961 | 0.007 | P10081 | Upper |
| 60S ribosomal protein L28 | 1.804 | 1.72E−04 | P02406 | Upper |
| 60S ribosomal protein L14-A | 1.614 | 5.05E−04 | P36105 | Lower |
| 40S ribosomal protein S24 | 1.481 | 0.007 | P26782 | Lower |

The molecular mechanisms underlying resveratrol's lifespan effect have been controversial (Howitz et al. (2003) *Nature* 425: 191-196; Kaeberlein et al. (2005) *J Biol Chem*

Figure 4D:
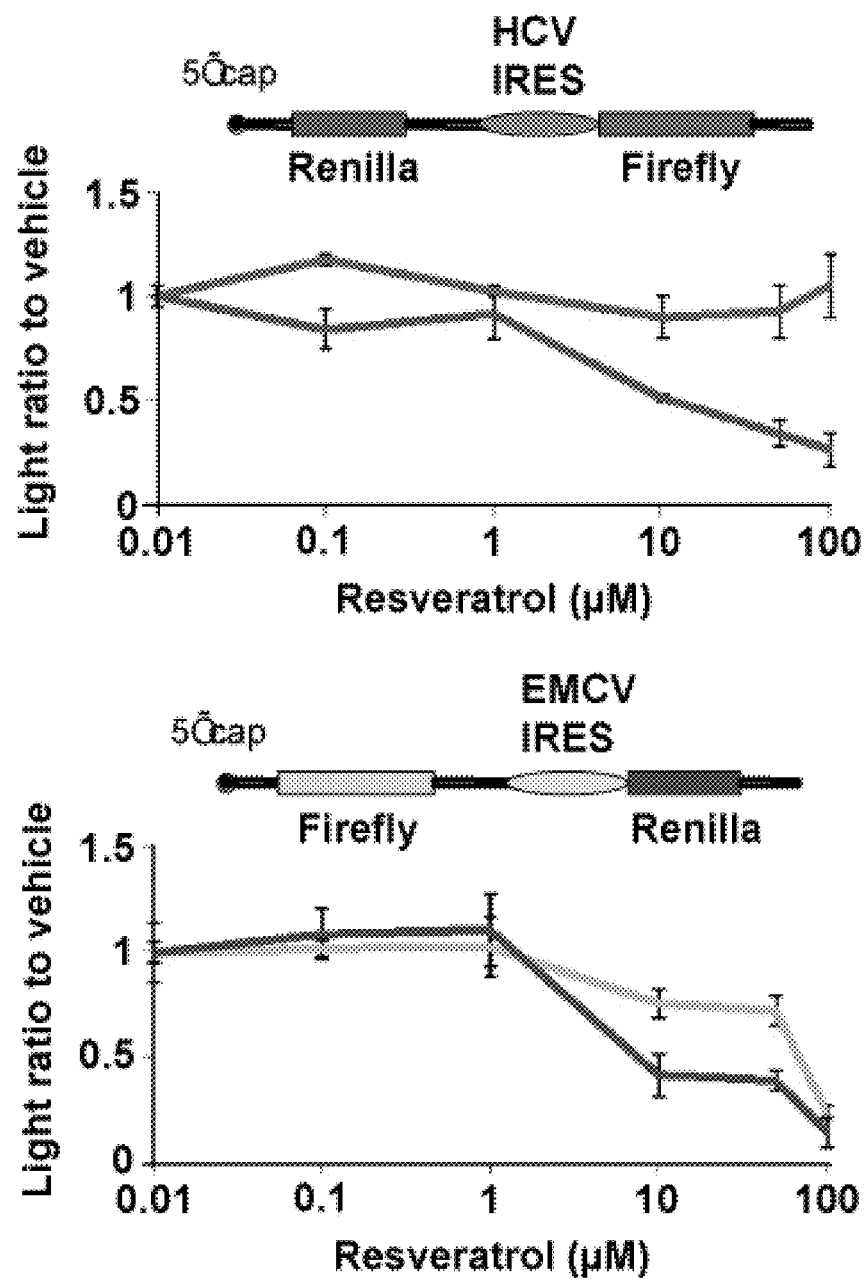

280: 17038-17045), and whether Sir2 serves as a direct target for resveratrol is an interesting problem that is being pursued. On the other hand, it is interesting to note that multiple genome-wide studies in *S. cerevisiae* and *C. elegans* have found knockouts or knockdowns of eIF4A and several ribosomal proteins to have significant increases in lifespan (Smith et al. (2008) *Genome Res* 18: 564-570). Our finding of resveratrol-mediated protection of eIF4A and ribosomal proteins by DARTS suggested that the protein translation machinery may be a molecular target of resveratrol in lifespan extension. To test this notion, we first asked whether resveratrol has a specific effect on protein translation. Using bicistronic dual-luciferase reporters to monitor cap-dependent translation (which requires initiation factors) and translation mediated by IRESs (which exhibit differing requirements for initiation factors), we found that cap-dependent translation and EMCV IRES-mediated translation, both of which require eIF4A, were inhibited in a dose-dependent manner by resveratrol, whereas translation from the eIF4A-independent, HCV IRES was unaffected (FIG. 4D). These results indicate that resveratrol specifically inhibits eIF4A- or eIF4G-dependent translation initiation, and does not impinge on other translation initiation factors or on translation elongation.

Figure 4E:
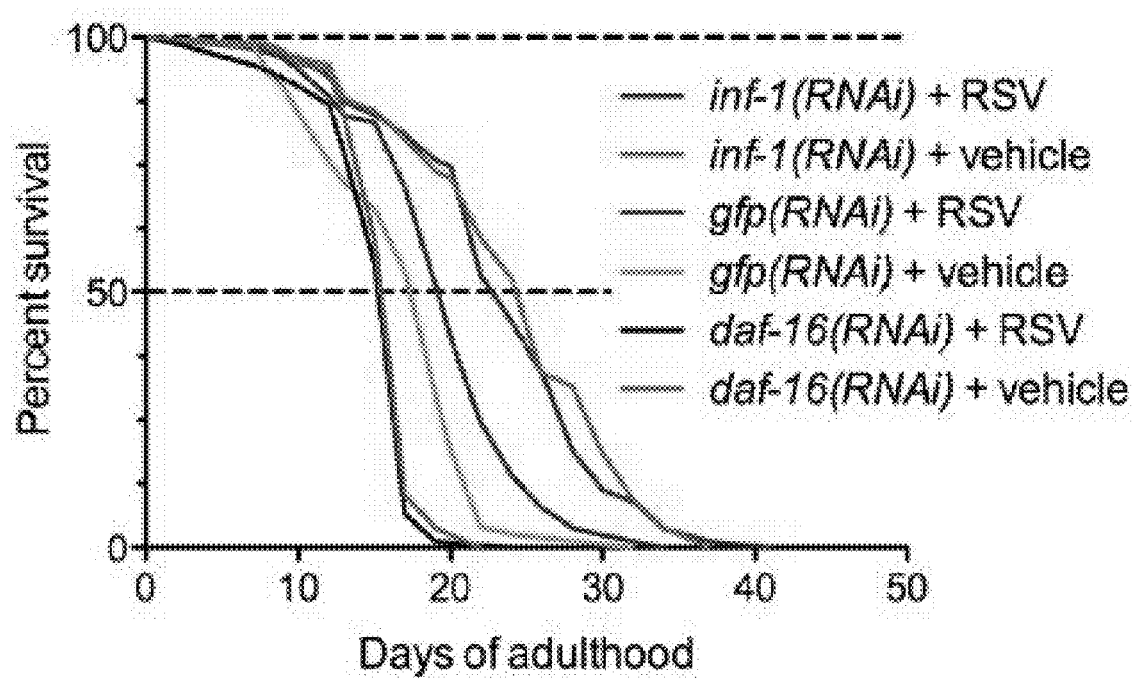

Finally, we asked whether eIF4A is required for resveratrol's longevity effect. Whereas resveratrol lengthens the lifespan of wild-type worms (FIG. 4E), as reported previously (Wood et al. (2004) *Nature* 430: 686-689), this longevity effect is lost in eIF4A knockdown worms (FIG. 4E), consistent with eIF4A being a physiological target of resveratrol. Interestingly, the longevity effect of resveratrol appears to require daf-16 (FIG. 4E), the Forkhead transcription factor which mediates lifespan extension by the insulin/IGF-1 pathway (Salih and Brunet (2008) *Curr Opin Cell Biol* 20: 126-136), reminiscent of its requirement for longevity in eIF4G knockdown animals (Hansen et al. (2007) *Aging Cell* 6: 95-110). Taken together, it is plausible that resveratrol increases lifespan by direct inhibition of translation initiation, through binding to eIF4A and/or one or more ribosomal proteins in the pre-initiation complex. However, this interpretation should be taken with an important caveat since the eIF4A-knockdown worms show a significantly enhanced lifespan (beyond the extension produced by resveratrol in wild-type worms). Furthermore, it is possible that knocking down an initiation factor like eIF4A will affect the expression level of many other proteins that could be targets. Our findings also point to eIF4A (and possibly other translation factors) as a new druggable target for anti-aging therapy. Several potent eIF4A inhibitors have recently been identified (Clardy (2006) *ACS Chem Biol* 1: 17-19).

DARTS Using Proteins Generated from cDNA.

Figure 5:
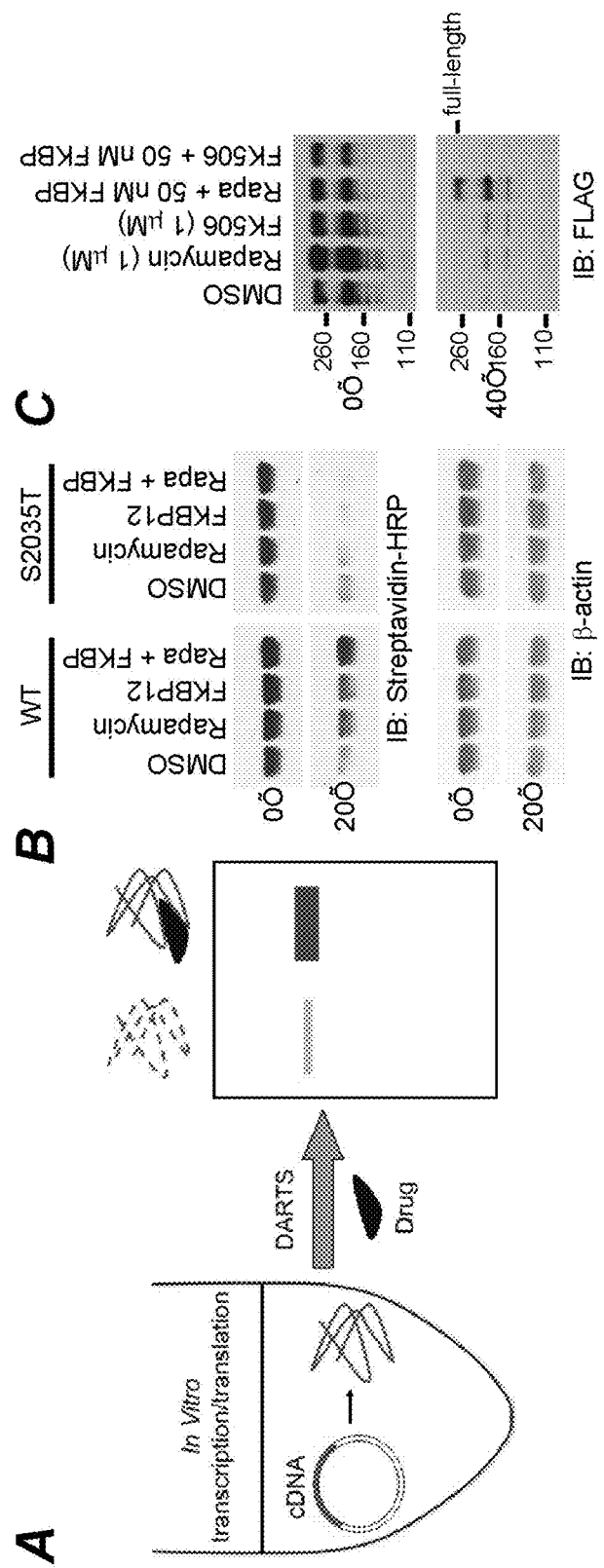
FIGS. 5A, 5B, and 5C illustrate DARTS using cDNAs.

The utility of DARTS in complex mixtures suggests that potential drug targets can be identified using a wide range of biological systems, and the method is unlimited by the availability and coverage of knock-out (or knock-down) libraries and genome arrays for model organisms. The limiting aspect of DARTS analysis is likely to be sensitivity of detection by mass spectrometry or other potential methods (as in affinity chromatography). This limitation is being increasingly alleviated with the development of more sensitive analytical tools. Nonetheless, we tested whether DARTS can be applied to a complementary unbiased platform, namely using proteins generated from cDNAs by in vitro transcription/translation (IVT) (FIG. 5A).

Reticulocyte lysate IVT is a powerful technique routinely employed in studies of protein function, and is readily adaptable to express proteins in a high-throughput manner (King et al. (1997) *Science* 277: 973-974). a test case, we used the human mTOR (mammalian target of rapamycin) protein, which is an important target (Bjornsti and Houghton (2004) *Nat Rev Cancer* 4: 335-348; Wullschleger et al. (2006) *Cell* 124: 471-484) and had been identified on the basis of its association with the FKBP12-rapamycin complex (see refs in Chen et al. (1995) *Proc. Natl. Acad. Sci.*, USA, 92: 4947-4951). As shown in FIG. 5B, an IVT mTOR fragment containing the FKBP-rapamycin binding domain (Chen et al. (1995) *Proc. Natl. Acad. Sci.*, USA, 92: 4947-4951) was protected from thermolysin digestion by the presence of FKBP12-rapamycin, whereas the S2035T-substituted mTOR that abolishes rapamycin binding (Id.) was not protected. IVT TOR proteins were labeled with biotin-Lys in this experiment, but other forms of amino acids could also be used. Alternatively, IVT proteins could be detected through an epitope tag without incorporation of any artificially labeled amino acids. For example, FLAG-tagged full-length mTOR protein was also a robust source of protein for the DARTS method (FIG. 5C). These results further demonstrate the versatility of DARTS and suggest nearly unlimited possibilities for screening cDNA libraries (Rolfs et al. (2008) *PLoS ONE* 3: e1528) and genome-wide collections of epitope-fused proteins (Ghaemmaghami et al. (2003) *Nature* 425: 737-741; Zhu et al. (2001) *Science* 293: 2101-2105) using DARTS to systematically analyze small-molecule-protein interactions.

Discussion

Developing new methods for drug target identification is an area of intense interest, and both experimental and computational approaches have been developed (Terstappen et al. (2007) *Nat Rev Drug Discov* 6: 891-903; Campillos et al. (2008) *Science* 321: 263-266). Previous methods for drug target identification have had substantial success, but many limitations remain. Traditionally, affinity chromatography has played a major role in the identification of the binding targets for many biologically active small molecules and natural products. In addition to affinity chromatography, many new methods for drug target identification have been developed, ranging from biochemistry, to genetics, proteomics, and imaging (Bharucha and Kumar (2007) *Comb Chem High Throughput Screen* 10: 618-634; Sleno and Emili (2008) *Curr Opin Chem Biol* 12: 46-54; Huang et al., (2004) *Proc. Natl. Acad. Sci.*, USA, 101: 16594-16599; Perlman et al. (2004) *Science* 306: 1194-1198; Eggert et al. (2004) *PLoS Biol* 2: e379; Cravatt et al. (2008) *Annu Rev Biochem* 77: 383-414; Ong et al. (2009) *Proc. Natl. Acad. Sci.*, USA, 106:4617-4622). All current target identification methods are of two main categories: affinity-based methods, which detect the direct binding of the drug to its target(s); and phenotype-based methods, which infer drug targets/pathways from physiological responses or biochemical signatures the drugs produce.

Advantages of DARTS.

Like affinity chromatography, DARTS relies on the affinity between a drug molecule and its protein target, and thereby is able to pinpoint direct binding partner(s) of the drug. One advantage of DARTS, however, is that because it does not require labeled ligands and instead uses "native" (i.e., unmodified) small molecules for binding, it is not limited by chemistry and can potentially be used to identify binding targets for any small molecule. Additionally, unlike cell-based methods, DARTS is completely independent of any effects of the drug on the system, and is therefore compatible with any mechanism of action, making it useful for any small molecule of interest. Moreover, DARTS can be performed using any cell or tissue type from any organism, and is thus not limited by the availability and coverage of knock-out (or knock-down) libraries and genome arrays for model organisms.

Once identified, potential drug targets can be confirmed by functional studies, and kinetics and affinities of the interactions can be measured using a variety of analytical methods. While biophysical methods (i.e., surface plasmon resonance, isothermal titration calorimetry, etc.) are traditionally used to analyze direct binding, DARTS proves to be a fast and robust method to determine direct binding of a small molecule (or metabolite) without requiring large amounts of pure protein, and is even amenable to using whole cell lysates.

Potential Limitations of the DARTS Method.

First, the binding affinity of the drug to its target may be a limiting factor. To date, our experiments suggest that DARTS is effective for molecules with inhibitory concentrations across many orders of magnitude, up to high-micromolar. Second, a potential fundamental limitation for DARTS is that a protein's susceptibility to proteolysis is determined by its conformational energy landscape, and it has been demonstrated that a small number of evolutionarily selected proteins (e.g., stress proteins) are quite refractory to protease digestion (Park et al. (2007) *J Mol Biol* 368: 1426-1437). Third, drug binding may change the protease susceptibility of non-target proteins, such as those that interact with or are part of complexes containing the target. But this result could be an advantage of the DARTS approach as well, insofar as it would provide information about protein complexes that are dissociated (or formed) upon drug binding. Drug binding in vivo might also increase proteolytic susceptibility of the target protein (Cohen et al. (2008) *Science* 322(5907): 1511-1516). This would—in the DARTS protocol—also identify target proteins of the small molecule being analyzed. A small-molecule effector that destabilizes a protein could, of course, also be identified by DARTS.

An extrinsic limiting aspect of DARTS analysis is likely to be sensitivity of detection by mass spectrometry (as in affinity chromatography). While DB-mediated protection of EF-1 alpha was visualized by eye on a stained gel in FIG. 3A, this will not necessarily be the case with many target proteins of lower abundance. Quantitative imaging or densitometry could prove useful with DARTS to assist in finding more subtle differences in protein abundance. Furthermore, proteomic techniques including 2D gels (Shevchenko et al. (1996) *Proc. Natl. Acad. Sci.*, USA, 93: 14440-14445), DIGE (Unlu et al. (1997) *Electrophoresis* 18: 2071-2077), and gel-free approaches like MudPIT (Wolters et al. (2001) *Anal Chem* 73: 5683-5690) would likely provide even greater sensitivity in conjunction with DARTS. Finally, the use of cDNA libraries to express proteins in cell culture or by IVT, as demonstrated in FIG. 5, also provides viable alternatives.

Effect of In Vivo Protein Stability on DARTS.

We rely on in vitro proteolysis using exogenous proteases in our DARTS method. Protein stability in vivo on the other hand is a much more complicated problem. Since degradation of proteins inside the cell is predominantly carried out by supramolecular machines known as the proteasomes and aggresomes, and is elaborately controlled by post-translational modifications such as phosphorylation and ubiquitinylation, protein stability in vivo is largely unpredictable. Indeed, in vivo stability of proteins upon drug/ligand binding is highly idiosyncratic in the literature; drug binding has been shown to both increase and decrease proteolytic susceptibility of the target protein (Stankunas et al. (2003) *Mol Cell* 12: 1615-1624; Cohen et al. (2008) *Science* 322(5907): 1511-1516; Banaszynski et al. (2006) *Cell* 126: 995-1004; Nishiya et al. (2009) *Anal Biochem* 385: 314-320. For instance, whereas unstable FRB domain and FKBP12 mutants are stabilized by the presence of ligands (Stankunas et al. (2003) *Mol Cell* 12: 1615-1624; Banaszynski et al. (2006) *Cell* 126: 995-1004) and topoisomerase-1 is destabilized by camptothecin (Cohen et al. (2008) *Science* 322(5907): 1511-1516), binding of estrogen receptor ligands each affects receptor stability differently (Wijayaratne and McDonnell (2001) *J Biol Chem* 276: 35684-35692). In any event, this information would be useful in conjunction with DARTS for elucidating the molecular mechanisms of action of drugs.

Additional Applications of DARTS.

Beyond drugs, we envisage that DARTS will also be useful for global mapping of protein-metabolite interaction networks and in elucidating potential protein targets for small molecules found in food or dietary supplements. DARTS may also be useful in identifying a wide range of small molecules that can be developed into a new genre of molecular imaging agents. Pharmaceutical agents almost always interact with the active sites of enzymes or the ligand binding sites of receptors. The design of most small-molecule molecular imaging probes usually begins with modification of the structure of known drugs. However, enzyme active sites and ligand binding sites represent only a very small percentage of the tertiary structures of target proteins. Small molecules that bind tightly and specifically to sites other than the active site or the ligand binding site on a protein, and are detectable by DARTS, would provide initial "hits" from which probes that can stoichiometrically measure protein concentrations by fluorescence, positron emission tomography, single photon emission tomography and other molecular imaging technologies could be developed through conventional medicinal chemistry or secondary chemical library procedures.

Materials and Methods

Reagents.

Recombinant human FKBP12 was purchased from R&D Systems (Cat. #3777-FK). The recombinant human FRAP1 (mTOR) fragment corresponding to amino acids 1360-2549 (163.9 kDa, ~70% purity) was obtained from Invitrogen (#PV4753). The proteases subtilisin Carlsberg (#P5380) and thermolysin (#88303) were purchased from Sigma. Stock solutions of each protease were made, aliquoted, and stored at −20° C. New aliquots were used for each proteolysis experiment. For Western blotting, anti-EF1A1 (Abcam #37969), anti-GAPDH (Ambion #4300), and anti-FLAG (Sigma) antibodies and the streptavidin-horseradish peroxidase conjugate (Streptavidin-HRP) from the Transcend Chemiluminescent Non-Radioactive Translation Detection System (Promega) were used. Coomassie and silver staining were performed using SimplyBlue and the SilverQuest staining kit from Invitrogen. Protein concentration was measured using the BCA protein assay kit (Pierce).

Plasmids.

The bicistronic translation reporter construct pcDNA/REN/HCV/FF was described previously (Bordeleau et al. (2006) *Nat Chem Biol* 2: 213-220). pcDNA/FF/EMCV/REN was generated by subcloning the XhoI-BamHI fragment from pKS/FF/EMCV/REN (Novac et al. (2004) *Nucleic Acids Res* 32: 902-915) into pcDNA3.1(−) using the same restriction sites.

For IVT, pcDNA3.1-hTOR1968C was generated by PCR cloning of mTOR coding region 5902-7650 (corresponding to hTOR aa 1968-2549) into pcDNA3.1 using the EcoRI and KpnI sites; the PCR template was a cDNA mixture that was synthesized by reverse transcription of total RNA isolated from HEK293 cells. pcDNA3.1-hTOR1968C/S2035T was generated similarly except using pBJ5-FLAG-FRAP/S2035T (Brown et al. (1995) *Nature* 377: 441-446) as PCR template. pcDNA3.1-FLAG-hTOR was generated by ligating a NotI-KpnI fragment (containing FLAG+mTOR coding region 1-5901) from pBJ5-FLAG-FRAP•S2035T (Id.) and a KpnI fragment with PCR'ed hTOR coding region 5902-7650 into pcDNA3.1 using the NotI and KpnI sites. All constructs were verified by DNA sequencing.

Darts with Complex Protein Mixtures.

Figure 3C:
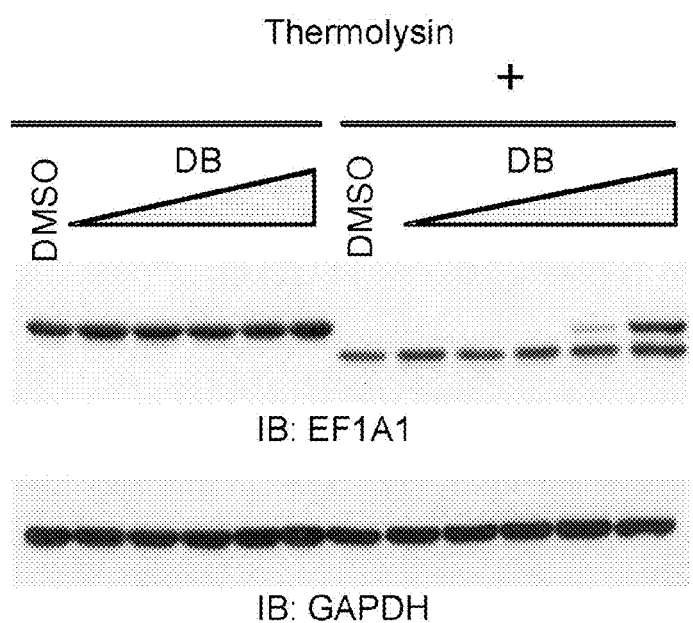

For FIGS. 3A and 3C, intact Jurkat cells were treated with DB from 100 pg/mL to 1 μg/mL or DMSO control for 30 min. Cells were lysed (without washing, in these experiments) with M-PER (Pierce) supplemented with protease and phosphatase inhibitors. After centrifugation (14,000 rpm, 15 min), lysates were diluted to the same final volume and protein concentration with M-PER and proteolysed in reaction buffer [50 mM Tris-HCl pH 8.0, 50 mM NaCl, 10 mM $CaCl_2$]. All steps were performed on ice or at 4° C. to help prevent premature protein degradation. Each sample was then quickly warmed to room temperature and proteolysed with 1 μg thermolysin for every 15 μg lysate for 10 min. To stop proteolysis, 0.5 M EDTA (pH 8.0) was added to each sample at a 1:10 ratio, mixed well, and placed on ice.

For DARTS using yeast cell lysates incubated in vitro with resveratrol (FIG. 4B), *S. cerevisiae* BY4742 cells were used.

Mass Spectrometry Analysis.

Gel bands were cut out and prepared for mass spec analysis with trypsin digestion as described in SI. Peptides were analyzed by LC/MS/MS on a Thermo LTQ-Orbitrap mass spectrometer with an Eksigent LC pump. For quantitative comparison of protein and peptide abundances, MS spectra were analyzed using the differential workflow of Rosetta Elucidator (Rosetta Inpharmatics) (54). Annotation was performed using PeptideTeller and ProteinTeller (see SI).

In Vivo Translation Assays.

HEK293 cells in DMEM+10% FBS were pre-treated with 50 μM resveratrol for 1 hr, and transfected with bicistronic translation reporter plasmids using LipoD293 DNA in vitro transfection reagent (SignaGen). 2 hr post-transfection, cells were washed with PBS, seeded in 96-well format and treated with resveratrol or vehicle control. Reporter activity was measured 33 hr post-transfection using the Dual-Glo luciferase assay system (Promega) with an Analyst HT plate reader (Molecular Devices).

We analyzed the effect of resveratrol on different luciferase assay systems using in vitro translated firefly luciferase, and found that the effect of resveratrol on firefly luciferase reaction is kit-dependent. For example, in the Bright-Glo kit (Promega #E2610), firefly luciferase readout is significantly decreased in the presence of resveratrol, as shown by (Bakhtiarova et al. (2006) *Biochem Biophys Res Commun* 351: 481-484). On the contrary, in the Dual-Glo kit (Promega #E2940), resveratrol has little or no inhibition on firefly luciferase readout. Our data in FIG. 4D were based on the Dual-Glo kit, in which the luciferase reaction is not affected by resveratrol. Also, there was no resveratrol added to the in vitro luciferase assay reactions in FIG. 4D. Rather, resveratrol was used to treat cells and washed away before the cells were lysed for luciferase assay.

*C. elegans* Lifespan Analysis.

N2 wild-type strains were maintained at 20° C. on standard nematode growth medium (NGM) seeded with *E. coli* OP50 as described (Brenner (1974) *Genetics* 77: 71-94). *E. coli* RNAi strains were obtained from Open Biosystems; clones were verified by sequencing. To make NGM plates containing resveratrol or vehicle, 240 μl of a solution containing 2.5 mM resveratrol (or the equivalent amount of ethanol, for vehicle control), 20% DMSO, 20% ethanol, 10% phosphate buffered saline (PBS), and 50% ddH20 were spread on top of the NGM plate, making a 50 μM final concentration of resveratrol in the plate. Resveratrol was dissolved in 95% ethanol and stored in 4° C.

Lifespan analysis was conducted with N2 worms at 20° C. Eggs were added to NGM plates containing OP50. At the L4 stage, worms were washed off and placed onto bacteria-less NGM plates for 60 min so that the worms can digest the remaining OP50 in their gut. Then worms were moved onto NGM plates containing gfp, daf-16, or inf-1 RNAi with resveratrol or vehicle. Ampicillin (50 μg/ml) and isopropyl β-D-thiogalactopyranoside (IPTG) (1 mM) were used to select for the RNAi *E. coli* and to induce the expression of dsRNA, respectively. Initially, 100 worms were picked for each treatment. During their egg-laying days, the worms were transferred to new plates every day, and then every other fourth day thereafter. To assess the survival of the worms, the animals were prodded with a platinum wire every other day, and those that failed to respond were scored as dead. Worms that died as a result of bagging or vulva bursting, as well as those that crawled off the plate, were not included in the study.

DARTS Using Proteins Generated by Rabbit Reticulocyte Lysate In Vitro Transcription/Translation (IVT) System.

For FIG. 5B, IVT was performed using Promega TnT T7 Quick Coupled Transcription/Translation System, with 0.5 μg of pcDNA3.1-hTOR1968C (encoding human mTOR aa 1968 to C-ter) or pcDNA3.1-hTOR1968C 52035T (encoding corresponding rapamycin-resistant mutant (Shevchenko et al. (1996) *Anal Chem* 68: 850-858)) vectors, and 2 μL of 8-biotin-Lys-tRNA (Transcend tRNA, Promega) in 50 μL reaction at 30° C. for 3 hr. DARTS was performed using 5 μL of translated lysate in 10 μL total reaction volume in [50 mM Tris-HCl pH 8.0, 50 mM NaCl, 10 mM $CaCl_2$], with 1 μM of rapamycin, 50 nM of FKBP12, or 50 nM FKBP12+1 μM rapamycin (pre-incubated on ice for 30 min to allow complex formation), and incubated on ice for 30 min. Proteolysis was performed with 2 ng thermolysin at room temperature for 20 min, and stopped with 1 μL of 0.5 M EDTA pH 8.0.

For FIG. 5C, N-terminal FLAG-tagged full-length human TOR protein was synthesized by IVT using 0.5 μg of pcDNA3.1-FLAG-hTOR vector in 50 μL reaction at 30° C. for 3 hr (Promega TnT T7 Quick Coupled Transcription/Translation System). DARTS was performed using 6 μL of translated lysate in 10 μL total reaction volume in reaction buffer [50 mM Tris-HCl pH 8.0, 50 mM NaCl, 10 mM CaCl2] with 1 μM of rapamycin or 1 μM of FK506, or co-treatment with 50 nM of FKBP12 (pre-incubated on ice for 30 min to allow complex formation), and incubated on ice for 45 min. Proteolysis was performed with 1 ng thermolysin at room temperature for 40 min, and stopped with 1 μL of 0.5 M EDTA pH 8.0.

Example 2

Supplemental/Supporting Information

Mass Spectrometry of DB-Bound, Proteolysis-Resistant Proteins in DARTS.

Mass spectrometry analysis of the protected band from FIG. 3A reveals significant enrichment (p-values<1.0E-45) of EF-1alpha isoforms (EEF1A1, 18.7 fold; EEF1A2, 21.7 fold). Although PGK1 and ENO1 levels were comparable to those of EF-1alpha, PGK1 enrichment was much lower (2.4 fold; p<1.0E-45) and ENO1 was slightly depleted (−1.8 fold; p=1.8E-42). The result could indicate lower affinity binding of DB to PGK1, or secondary effects on protein abundance because in this experiment the cells were treated with drug in vivo. SUCLA2 (11.7 fold) and BAT1 (7.5 fold) were enriched intermediately (and possibly indirectly as well because of the in vivo treatment), but since they were >100 times less abundant than EF-1alpha they could not account for the increase in the protected band intensity.

DARTS Using Different Proteases.

The proteome encodes a wide range of susceptibility to proteolysis, and each protein has its own unique resistance signature against a panel of proteases. We found that although thermolysin worked well for DARTS with many target proteins, its weakness lied in the fact that a significant proportion of the proteome is highly resistant to proteolysis by thermolysin, even after allowing the digestion to proceed for several hours or overnight. This is consistent with previously published observations (Park et al. (2007) *J Mol Biol* 368: 1426-1437), and in effect limits the utility of thermolysin as an enzyme for DARTS.

Our effort to overcome the limitations of thermolysin initially led us to try subtilisin. In our hands subtilisin could be used successfully with DARTS for several target proteins (FIG. 2B and FIG. 9). Additionally, subtilisin proved to be much more robust than thermolysin, and was able to digest almost all proteins into smaller fragments and peptides at much lower concentrations than thermolysin. However, the magnitude of protection of the target protein achievable with subtilisin appeared to be less than with thermolysin. This could be explained by the ability of subtilisin to proteolyse native, folded proteins, whereas thermolysin requires its substrates to be unfolded. Alternatively, the substrate residues of subtilisin may simply have been more accessible in the structures of the target proteins tested than those of thermolysin, and different results would be seen with other proteins.

Figure 9A:
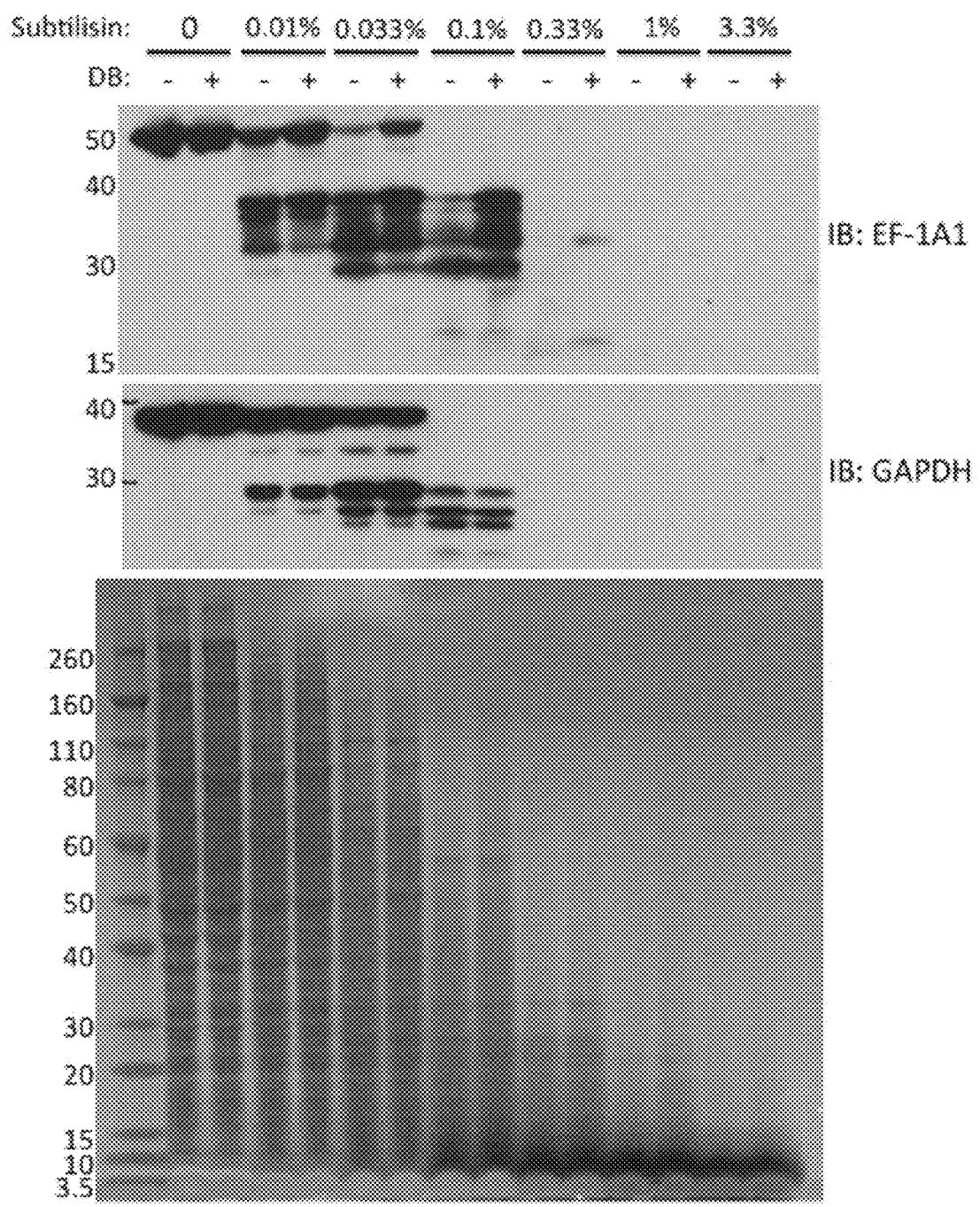
FIG. 9A illustrates DARTS using subtilisin. Lysates from untreated human Jurkat cells were incubated with DMSO control or DB (1 μg/mL) for 1 hr at room temperature. Each sample was then split into seven aliquots, which underwent digestion with various concentrations of subtilisin, relative to the total amount of protein per sample, for 30 min at room temperature. Digestion was stopped by adding 5× sample loading buffer and boiling immediately. Half of each sample was then loaded onto one of two 4-12% SDS-PAGE gels for SimplyBlue staining and western blotting.
Figure 9B:
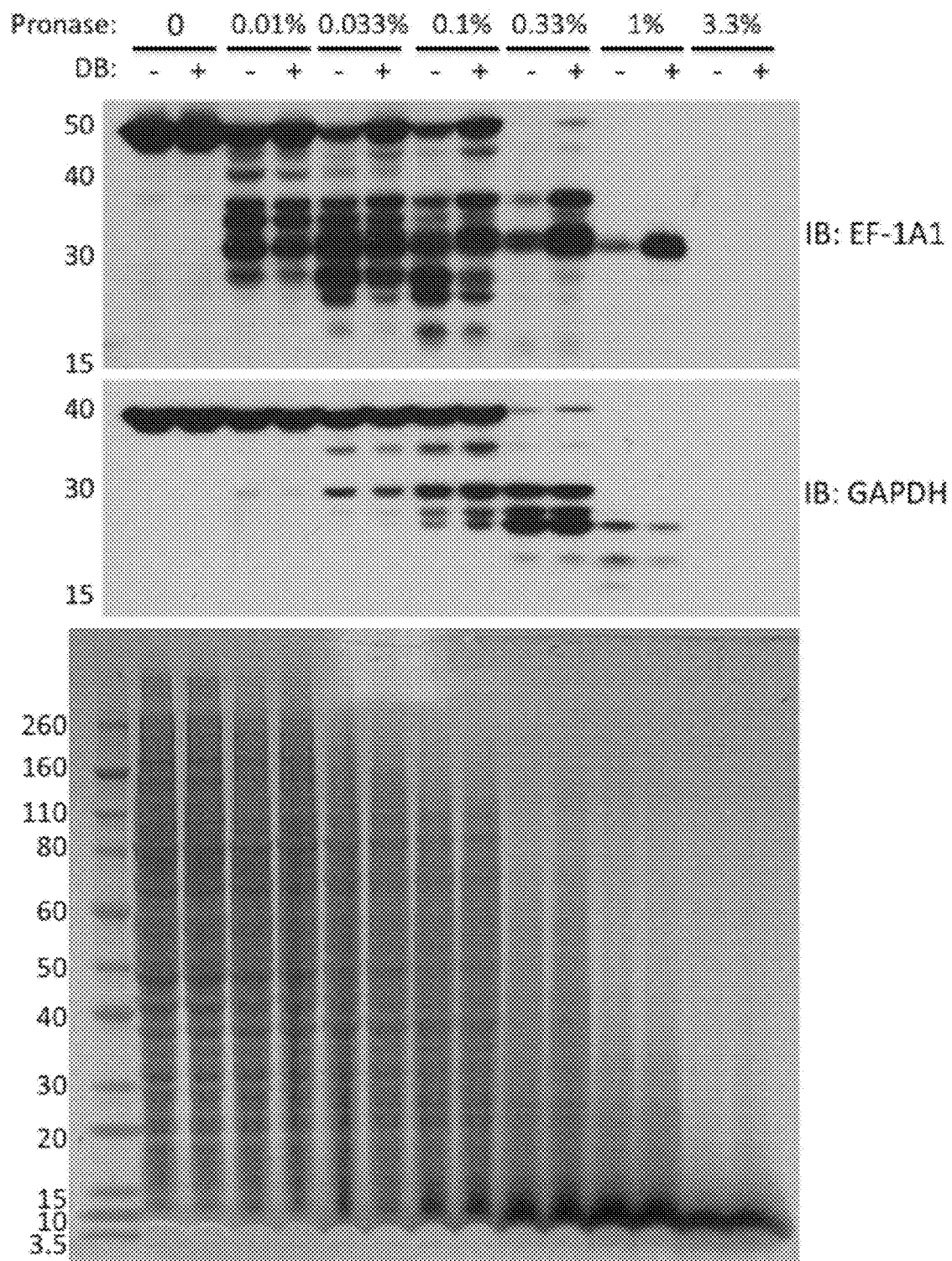
FIG. 9B illustrates DARTS using pronase. Lysates from untreated human Jurkat cells were incubated with DMSO control or DB (1 μg/mL) for 1 hr at room temperature. Each sample was then split into seven aliquots, which underwent digestion with various concentrations of PRONASE®, relative to the total amount of protein per sample, for 30 min at room temperature. Digestion was stopped by adding 5× sample loading buffer and boiling immediately. Half of each sample was then loaded onto one of two 4-12% SDS-PAGE gels for SimplyBlue staining and western blotting.

As an alternative to using a single protease, we hypothesized that perhaps a mixture of many different enzymes would provide the best overall digestion efficiency and magnitude of target protein protection. To test this we initially chose to use pronase (Roche), a commercially available protease mixture containing endo- and exo-proteases capable of digesting native and unfolded proteins. As seen in FIG. 9B, pronase was able to achieve a similar overall level of digestion as subtilisin at various concentrations, while permitting a more pronounced protective effect of EF-1A by DB. These results suggest that pronase or other protease mixtures may prove to be most useful for DARTS, given its ability to break down virtually all proteins into individual amino acids at sufficiently high concentrations.

Resveratrol Target Analysis.

For cytotoxic and cytostatic small molecules, deletion mutants in their target often would have increased sensitivity to the drug (and overexpression could decrease sensitivity). Indeed, this is the basis for the elegant haploinsufficiency profiling (HIP) strategy (Giaever et al. (1999) *Nat Genet*. 21: 278-283). However, an inherent limitation of this type of fitness-based methods is that they are applicable only to drugs that affect cell growth/viability, i.e., cytotoxic or cytostatic drugs. Resveratrol, just like most bioactive food compounds, exhibits very low potency and causes no detectable cytotoxicity even at saturating concentrations. In fact, resveratrol added at a final concentration of ~1 mM precipitated out of the culture medium but did not cause detectable inhibition of yeast growth—not in the wild type, nor in tif1 or tif2 deletion mutants (FIG. 10). A key advantage of DARTS is that it is independent of the drug's biological phenotype, and thus is not limited to the studies of cytotoxic/cytostatic drugs or drugs that induce transcriptional or morphological changes which have been the limitation of previous methods.

Supplemental Materials and Methods.

DARTS with Pure Proteins.

For FIG. 2B, 40 ng/µL (~3 µM) recombinant FKBP12 was incubated with rapamycin, FK506, wortmannin (100 µM each), or DMSO solvent control for 2 hr at 4° C., followed by digestion with subtilisin at room temperature. Proteolysis 1, 1:100 (wt:wt) subtilisin:FKBP12 for 3 hours; Proteolysis 2, 1:10 (wt:wt) subtilisin:FKBP12 for 30 min. For FIG. 2C, 200 ng of recombinant FRAP1 (mTOR) was incubated with E4 or DMSO solvent control for 30 min at 4° C., followed by digestion with 20 ng thermolysin for 1 hr at room temperature.

Sample Preparation for Mass Spectrometry.

Bands from 1D SDS-PAGE gels were cut out and prepared for mass spec analysis as described previously (Brown et al. (1995) *Nature* 377: 441-446; Shevchenko et al. (1996) *Anal Chem* 68: 850-858). Briefly, each band was destained by washing twice in 200 µl 50 mM $NH_4HCO_3$, 50% acetonitrile for 15 min with slow vortexing, followed by dehydrating with 100 µl 100% acetonitrile and drying by speedvac. Reduction was performed with 30 µl 10 mM DTT, 10 mM TCEP for 30 min at 56° C. The bands were then washed with 100 µl 50 mM $NH_4HCO_3$, 50% acetonitrile and dehydrated with 100 µl 100% acetonitrile. Alkylation was performed with 100 µl 100 mM iodoacetamide for 30 min in the dark, followed by washing twice in 200 µl 50 mM $NH_4HCO_3$, 50% acetonitrile for 2 min with slow vortexing. The bands were then dehydrated with 200 µl 100% acetonitrile and dried by speedvac.

Each band was rehydrated in 30 µl 50 mM $NH_4HCO_3$ pH 8.0 containing 20 trypsin on ice for 15 min. Remaining trypsin solution was replaced with 30 µl 50 mM $NH_4HCO_3$ pH 8.0. In-gel tryptic digestion was then performed overnight at 37° C. Digestion was halted with 5 µl 5% aqueous TFA. Peptides were extracted by shaking the solution for 15 min, saving the solution, and replacing with 30 µl 50% acetonitrile, 0.1% TFA and shaking for 15 min twice. The extracted peptides were then concentrated to 25 µl by speedvac.

Mass Spectrometry.

Tryptic peptides were analyzed by LC/MS/MS on a Thermo LTQ-Orbitrap mass spectrometer with an Eksigent LC pump. The peptides were loaded onto a C18 reverse-phase column at a flow rate of 3 µl/min. Mobile phase A was 0.1% formic acid and 2% ACN in water; mobile phase B was 0.1% formic acid and 20% water in ACN. Peptides were eluted from the column at a flow rate of 220 nl/min using a linear gradient from 5% B to 50% B over 60 min, then to 95% B over 5 min, and finally keeping constant 95% B for 5 min. Spectra were acquired in data-dependent mode (using dynamic exclusion of 30 sec for fragmented peptides) with the Orbi-trap used for MS scans and LTQ for MS/MS scans.

Proteins were initially identified by searching the spectra against the human International Protein Index database (version 3.46) and the *S. cerevisiae* Swissprot database (May 2008) using the SEQUEST algorithm (Eng et al. (1994) *J Am Soc Mass Spectrom* 5: 976-989) integrated into the Bioworks software package. Each peptide met the following criteria: XCorr ≥2 (+1), ≥3 (+2), ≥4 (+3), ≥5 (+4), and DeltaCN>0.1. For quantitative comparison of protein and peptide abundances, MS spectra were analyzed using the differential workflow of the Rosetta Elucidator software system (Rosetta Inpharmatics) (Neubert et al. (2008) *J Proteome Res* 7: 2270-2279). Annotation was performed using PeptideTeller and ProteinTeller with a minimum probability of 0.99 and predicted error of 0.0. Protein ratio data were generated with a P-value cutoff of 0.01 for all proteins with a peptide number >1. Intensity scaling was performed against the mean of feature signals, with 10% of outliers removed from the baseline dataset. Similar results were obtained in analysis without intensity scaling (FIG. 9A). Analysis of a control band from the same gel in the Didemnin B experiment that stained at the same intensity in both lanes revealed no significant differences in protein levels (FIG. 9B).

DARTS Using Cell Lysates Incubated In Vitro with Didemnin B.

For FIG. 7, human Jurkat cells were lysed in M-PER (Pierce) supplemented with protease and phosphatase inhibitors. Protein concentration was determined by BCA Protein Assay kit (Pierce). Lysates were incubated with DMSO control, or DB from 1 ng/mL to 1 µg/mL, for 30 min at room temperature. Samples were then divided into two aliquots, each of which underwent proteolysis with thermolysin or mock proteolysis, respectively, followed by western blot analysis.

DARTS Using Yeast Cell Lysates.

Figure 8C:
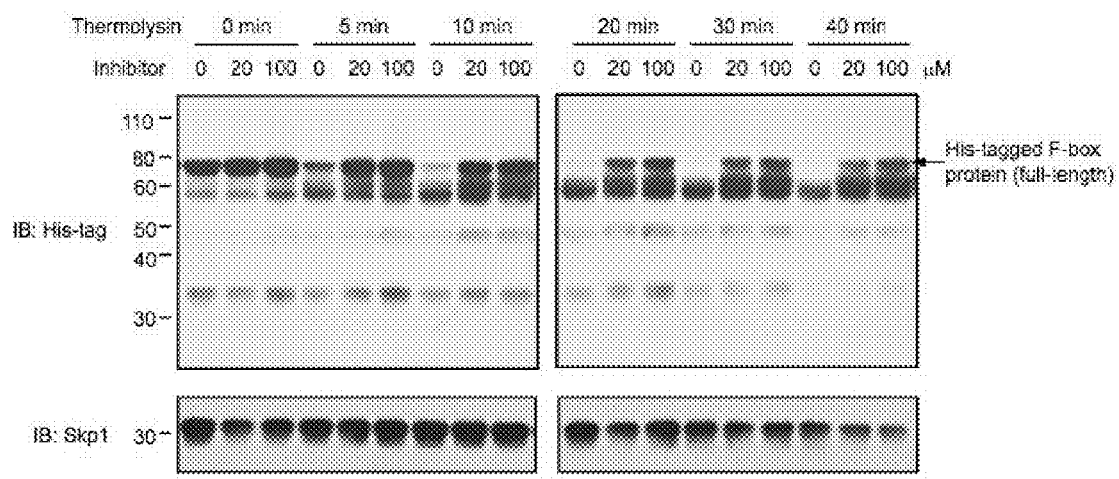
FIG. 8C illustrates DARTS using an SCF ubiquitin E3 ligase inhibitor identified from a phenotype-based chemical genetic screen. Yeast cells expressing RGS6H-tagged F-box protein were cultured to mid-log phase ($1.0 \times 10^7$ cells/mL) and treated with the inhibitor at indicated concentrations for 45 min. Then cells were pelleted, washed once with water, and lysed in Triton-lysis buffer with FAST-PREP®. Protein concentration of the lysate was measured using BCA Protein Assay kit (Pierce). For DARTS, 54 μg of lysate was used in 10 μL (total) reaction. For proteolysis, 20 ng of thermolysin was used for one reaction. The E3 inhibitor protects the F-box protein, but not an associated Skp1 protein, from protease digestion.

For FIG. 8C, yeast cells expressing a His-tagged F-box protein were cultured to mid-log phase ($1.0 \times 10^7$ cells/mL) and treated with the SCF ubiquitin E3 ligase inhibitor at indicated concentrations for 45 min. Then cells were pelleted, washed once with water, and lysed in Triton-lysis buffer with FastPrep. Protein concentration of the lysate was measured using BCA Protein Assay kit (Pierce). For DARTS, 54 µg of lysate was used in 10 µl, (total) reaction. For proteolysis, 20 ng of thermolysin was used for one reaction.

For the DARTS experiment using yeast cell lysates incubated in vitro with resveratrol, BY4742 cells were suspended in yeast extraction buffer (Grant et al. (1999) Meth. Mol Biol 119: 311-317) [(40 mM HEPES/KOH pH 7.5, 350 mM NaCl, 0.5 mM DTT, 10% glycerol, 0.1% Tween-20) supplemented with Roche complete protease inhibitor cocktail (Roche Diagnostics, Indianapolis, Ind.)]. Cell pellets were broken with glass beads for 2×40 s at 4° C. in a FastPrep-24 (MP Biomedicals, Solon, Ohio). Whole cell lysates were collected after centrifugation (1500 rpm, 10 min). Lysates were incubated with ethanol control or 1 mM resveratrol for 30 min at room temperature. Samples were then divided into two aliquots, which underwent proteolysis with thermolysin or mock proteolysis.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of identifying a protein target that interacts with or is bound by a test agent, said method comprising:
    contacting a test sample comprising a plurality of proteins with said test agent to form a sample/test agent mixture;
    contacting said mixture with a protease where said protease is not said test agent;
    determining the abundance of a protein in said test sample/test agent mixture and in a negative control sample lacking said test agent; and
    identifying and/or selecting a protein or protein fragment that is protected from proteolysis, wherein said identifying comprises comparing the abundance of a protein in said test sample/test agent mixture to the abundance of a protein in said negative control sample, and the presence and/or abundance of a protein or protein fragment protected from proteolysis in said test sample is an indicator that said protein or protein fragment binds to or interacts with said test agent and is a target for said test agent.

2. The method of claim 1, wherein said test sample comprises recombinantly expressed proteins.

3. The method of claim 1, wherein said test sample comprises a cell or tissue lysate.

4. The method of claim 3, wherein said cell or tissue lysate is from a healthy cell or tissue.

5. The method of claim 3, wherein said cell or tissue lysate is from a diseased cell or tissue.

6. The method of claim 3, wherein said cell or tissue lysate is from a cell or tissue having a mutated genome.

7. The method of claim 1, wherein said test sample comprises a plurality of proteins selected from the group consisting of a human protein, a non-human mammalian protein, an insect protein, a fungal protein, an algal protein, a plant protein, a bacterial protein, and a viral protein.

8. The method of claim 1, wherein said test sample comprises in vitro translated protein(s).

9. The method of claim 8, wherein said in vitro translated proteins are produced in a system selected from the group consisting of a reticulolycte cell-free system, a wheat germ cell free system, and an E. coli cell free system.

10. The method of claim 1, wherein said protease comprises a protease selected from the group consisting of a serine protease, a threonine protease, a cysteine protease, an aspartate protease, a metalloprotease, and a glutamic acid protease.

11. The method of claim 1, wherein said protease comprises a mixture of one or more endopeptidases and exopeptidases.

12. The method of claim 1, wherein said protease comprises subtilisin or thermolysin.

13. The method of claim 1, wherein said protease comprises pronase.

14. The method of claim 1, wherein said identifying comprises a method selected from the group consisting of a 1D electrophoresis, a 2-D electrophoresis, a chromatography, a capillary electrophoresis, a Western blot, and a mass spectrograph.

15. The method of claim 1, wherein said identifying comprises 1D or 2D SDS PAGE and staining.

16. The method of claim 15, wherein said method further comprises removing a band of the SDS page gel that shows altered protein abundance and performing mass spectrograph on the protein from said band.

17. The method of claim 1, wherein said test agent is a human or veterinary pharmaceutical.

18. The method of claim 1, wherein said test agent is selected from the group consisting of a metabolite, a herbal or other plant extract, a food component, a food additive, an agricultural pesticide or herbicide, a preservative, a colorant, a fragrance, an environmental agent, and a nanoparticle.

19. A method of identifying a protein target that interacts with or is bound by a test agent, said method comprising:
    contacting a test sample comprising a plurality of proteins with said test agent to form a sample/test agent mixture;
    contacting said mixture with a protease where said protease is not said test agent;
    determining the abundance of a protein in said test sample/test agent mixture and in a negative control sample lacking said test agent; and
    identifying and/or selecting a protein or protein fragment whose proteolysis is increased, wherein said identifying comprises comparing the abundance of a protein in said test sample/test agent mixture to the abundance of a protein in said negative control sample where an increase in proteolysis of a protein or protein fragment in said test sample is an indicator that said protein or protein fragment binds to or interacts with said test agent and is a target for said test agent.

20. The method of claim 19, wherein said test sample comprises recombinantly expressed proteins.

21. The method of claim 19, wherein said test sample comprises a cell or tissue lysate.

22. The method of claim 21, wherein said cell or tissue lysate is from a healthy cell or tissue.

23. The method of claim 21, wherein said cell or tissue lysate is from a diseased cell or tissue.

24. The method of claim 21, wherein said cell or tissue lysate is from a cell or tissue having a mutated genome.

25. The method of claim 19, wherein said test sample comprises one or more proteins selected from the group consisting of a human protein, a non-human mammalian protein, an insect protein, a fungal protein, an algal protein, a plant protein, a bacterial protein, and a viral protein.

26. The method of claim 19, wherein said test sample comprises in vitro translated protein(s).

27. The method of claim 26, wherein said in vitro translated proteins are produced in a system selected from the group consisting of a reticulolycte cell-free system, a wheat germ cell free system, and an *E. coli* cell free system.

28. The method of claim 19, wherein said protease comprises a protease selected from the group consisting of a serine protease, a threonine protease, a cysteine protease, an aspartate protease, a metalloprotease, and a glutamic acid protease.

29. The method of claim 19, wherein said protease comprises a mixture of one or more endopeptidases and exopeptidases.

30. The method of claim 19, wherein said protease comprises subtilisin or thermolysin.

31. The method of claim 19, wherein said protease comprises pronase.

32. The method of claim 19, wherein said identifying comprises a method selected from the group consisting of a 1D electrophoresis, a 2-D electrophoresis, a chromatography, a capillary electrophoresis, a Western blot, and a mass spectrograph.

33. The method of claim 19, wherein said identifying comprises 1D or 2D SDS PAGE and staining.

34. The method of claim 33, wherein said method further comprises removing a band of the SDS page gel that shows altered protein abundance and performing mass spectrograph on the protein from said band.

35. The method of claim 19, wherein said test agent is a human or veterinary pharmaceutical.

36. The method of claim 19, wherein said test agent is selected from the group consisting of a metabolite, a herbal or other plant extract, a food component, a food additive, an agricultural pesticide or herbicide, a preservative, a colorant, a fragrance, an environmental agent, and a nanoparticle.

* * * * *